United States Patent
Marecki et al.

(10) Patent No.: US 9,848,795 B2
(45) Date of Patent: Dec. 26, 2017

(54) ELECTRODE ASSEMBLY

(71) Applicant: BOSTON SCIENTIFIC SCIMED, INC., Maple Grove, MN (US)

(72) Inventors: Andrew T. Marecki, Shrewsbury, MA (US); Paul Hultz, Brookline, MA (US); Michael C. Kozlowski, Wakefield, MA (US); Brian Stewart, North Reading, MA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 244 days.

(21) Appl. No.: 14/723,408

(22) Filed: May 27, 2015

(65) Prior Publication Data

US 2015/0351652 A1 Dec. 10, 2015

Related U.S. Application Data

(60) Provisional application No. 62/007,716, filed on Jun. 4, 2014.

(51) Int. Cl.
*A61B 5/042* (2006.01)
*A61B 18/14* (2006.01)
(Continued)

(52) U.S. Cl.
CPC .......... *A61B 5/0422* (2013.01); *A61B 5/6856* (2013.01); *A61B 5/6858* (2013.01); *A61B 5/6859* (2013.01); *A61B 18/1492* (2013.01); *A61B 5/6855* (2013.01); *A61B 5/6857* (2013.01); *A61B 2017/00044* (2013.01); *A61B 2018/0016* (2013.01); *A61B 2018/00267* (2013.01); *A61B 2562/0209* (2013.01); *A61B 2562/125* (2013.01); *A61B 2562/164* (2013.01);
(Continued)

(58) Field of Classification Search
CPC ... A61B 5/0422; A61B 5/6859; A61B 5/6869; A61B 2018/00267
See application file for complete search history.

(56) References Cited

U.S. PATENT DOCUMENTS

| 4,649,924 A | 3/1987 | Taccardi |
| 4,674,518 A | 6/1987 | Salo |

(Continued)

FOREIGN PATENT DOCUMENTS

| CA | 2719329 A1 | 10/2009 |
| CN | 203017083 U | 6/2013 |

(Continued)

OTHER PUBLICATIONS

Lorensen et al., "Marching Cubes: A High Resolution 3D Surface Construction Algorithm", Computer Graphics 21 (4):163-169, Jul. 1987.

(Continued)

*Primary Examiner* — Lee S Cohen
(74) *Attorney, Agent, or Firm* — Faegre Baker Daniels LLP

(57) ABSTRACT

An expandable electrode assembly for use in a cardiac mapping procedure includes multiple bipolar electrode pairs including a first electrode located on an outer surface and a second electrode located on an inner surface of the individual splines forming the expandable electrode assembly. Such an electrode arrangement may produce improved electrical activation signals which may be used to produce a more accurate map of the electrical activity of a patient's heart.

18 Claims, 15 Drawing Sheets

(51) Int. Cl.
*A61B 5/00* (2006.01)
*A61B 17/00* (2006.01)
*A61B 18/00* (2006.01)

(52) U.S. Cl.
CPC .... *A61B 2562/166* (2013.01); *Y10T 29/49119* (2015.01); *Y10T 29/49126* (2015.01)

(56) References Cited

U.S. PATENT DOCUMENTS

| | | |
|---|---|---|
| 4,840,182 A | 6/1989 | Carlson |
| 4,920,490 A | 4/1990 | Isaacson |
| 5,156,151 A | 10/1992 | Imran |
| 5,284,142 A | 2/1994 | Goble et al. |
| 5,297,549 A | 3/1994 | Beatty et al. |
| 5,300,068 A | 4/1994 | Rosar et al. |
| 5,309,910 A | 5/1994 | Edwards et al. |
| 5,341,807 A | 8/1994 | Nardella |
| 5,381,333 A | 1/1995 | Isaacson et al. |
| 5,456,254 A | 10/1995 | Pietroski et al. |
| 5,469,858 A | 11/1995 | Osborne |
| 5,480,422 A | 1/1996 | Ben-Haim |
| 5,499,981 A | 3/1996 | Kordis |
| 5,500,011 A | 3/1996 | Desai |
| 5,553,611 A | 9/1996 | Budd et al. |
| 5,568,809 A | 10/1996 | Ben-Haim |
| 5,577,502 A | 11/1996 | Darrow et al. |
| 5,588,429 A | 12/1996 | Isaacson et al. |
| 5,634,469 A | 6/1997 | Bruder et al. |
| 5,662,108 A | 9/1997 | Budd et al. |
| 5,687,737 A | 11/1997 | Branham et al. |
| 5,697,377 A | 12/1997 | Wittkampf |
| 5,704,365 A | 1/1998 | Albrecht et al. |
| 5,722,402 A | 3/1998 | Swanson et al. |
| 5,782,239 A | 7/1998 | Webster et al. |
| 5,840,025 A | 11/1998 | Ben-Haim |
| 5,840,031 A | 11/1998 | Crowley |
| 5,846,198 A | 12/1998 | Killmann |
| 5,848,972 A | 12/1998 | Triedman et al. |
| 5,871,443 A | 2/1999 | Edwards et al. |
| 5,893,847 A | 4/1999 | Kordis |
| 5,896,847 A | 4/1999 | Usuki |
| 5,921,982 A | 7/1999 | Lesh et al. |
| 5,928,228 A | 7/1999 | Kordis et al. |
| 5,928,239 A | 7/1999 | Mirza |
| 5,954,665 A | 9/1999 | Ben-Haim |
| 5,971,933 A | 10/1999 | Gopakumaran et al. |
| 5,983,126 A | 11/1999 | Wittkampf |
| 5,986,126 A | 11/1999 | Bunel et al. |
| 6,014,581 A | 1/2000 | Whayne et al. |
| 6,050,267 A | 4/2000 | Nardella et al. |
| 6,095,150 A | 8/2000 | Panescu et al. |
| 6,163,716 A | 12/2000 | Edwards et al. |
| 6,167,296 A | 12/2000 | Shahidi |
| 6,226,542 B1 | 5/2001 | Reisfeld |
| 6,236,886 B1 | 5/2001 | Cherepenin et al. |
| 6,240,307 B1 | 5/2001 | Beatty et al. |
| 6,246,898 B1 | 6/2001 | Vesely et al. |
| 6,254,536 B1 | 7/2001 | DeVito |
| 6,278,894 B1 | 8/2001 | Salo et al. |
| 6,298,257 B1 | 10/2001 | Hall et al. |
| 6,308,093 B1 | 10/2001 | Armoundas et al. |
| 6,314,310 B1 | 11/2001 | Ben-Haim et al. |
| 6,317,619 B1 | 11/2001 | Boernert et al. |
| 6,318,375 B1 | 11/2001 | Plicchi et al. |
| 6,360,123 B1 | 3/2002 | Kimchi et al. |
| 6,368,285 B1 | 4/2002 | Osadchy et al. |
| 6,400,981 B1 | 6/2002 | Govari |
| 6,516,807 B1 | 2/2003 | Panescu et al. |
| 6,547,082 B1 | 4/2003 | Babini |
| 6,556,695 B1 | 4/2003 | Packer et al. |
| 6,574,492 B1 | 6/2003 | Ben-Haim et al. |
| 6,574,498 B1 | 6/2003 | Gilboa |
| 6,593,884 B1 | 7/2003 | Gilboa et al. |
| 6,600,948 B2 | 7/2003 | Ben-Haim et al. |
| 6,603,996 B1 | 8/2003 | Beatty et al. |
| 6,631,290 B1 | 10/2003 | Guck et al. |
| 6,640,119 B1 | 10/2003 | Budd et al. |
| 6,650,927 B1 | 11/2003 | Keidar |
| 6,690,963 B2 | 2/2004 | Ben-Haim et al. |
| 6,701,176 B1 | 3/2004 | Halperin et al. |
| 6,728,562 B1 | 4/2004 | Budd et al. |
| 6,773,402 B2 | 8/2004 | Govari et al. |
| 6,807,439 B2 | 10/2004 | Edwards et al. |
| 6,839,588 B1 | 1/2005 | Rudy |
| 6,847,839 B2 | 1/2005 | Ciaccio et al. |
| 6,872,428 B2 | 3/2005 | Yang et al. |
| 6,892,090 B2 | 5/2005 | Verard et al. |
| 6,892,091 B1 | 5/2005 | Ben-Haim et al. |
| 6,893,588 B2 | 5/2005 | Lawson et al. |
| 6,939,309 B1 | 9/2005 | Beatty et al. |
| 6,957,101 B2 | 10/2005 | Porath et al. |
| 6,978,168 B2 | 12/2005 | Beatty et al. |
| 6,990,370 B1 | 1/2006 | Beatty et al. |
| 7,016,719 B2 | 3/2006 | Rudy et al. |
| 7,043,292 B2 | 5/2006 | Tarjan et al. |
| 7,198,635 B2 | 4/2007 | Danek et al. |
| 7,263,397 B2 | 8/2007 | Hauck et al. |
| 7,505,810 B2 | 3/2009 | Harlev et al. |
| 7,515,954 B2 | 4/2009 | Harlev et al. |
| 7,729,752 B2 | 6/2010 | Harlev et al. |
| 8,103,327 B2 | 1/2012 | Harlev et al. |
| 8,137,343 B2 | 3/2012 | Harlev et al. |
| 8,364,235 B2 | 1/2013 | Kordis et al. |
| 8,447,377 B2 | 5/2013 | Harlev et al. |
| 8,463,368 B2 | 6/2013 | Harlev et al. |
| 8,538,509 B2 | 9/2013 | Harlev et al. |
| 8,725,240 B2 | 5/2014 | Harlev et al. |
| 8,728,075 B2 | 5/2014 | Wu et al. |
| 8,755,861 B2 | 6/2014 | Harlev et al. |
| 8,825,130 B2 | 9/2014 | Just et al. |
| 9,014,793 B2 | 4/2015 | Harlev et al. |
| 9,585,588 B2 | 3/2017 | Marecki et al. |
| 9,687,166 B2 | 6/2017 | Subramaniam et al. |
| 2002/0151807 A1 | 10/2002 | Goldin |
| 2002/0177766 A1 | 11/2002 | Mogul |
| 2003/0018251 A1 | 1/2003 | Solomon |
| 2003/0065271 A1 | 4/2003 | Khoury |
| 2003/0076277 A1 | 4/2003 | Muramatsu et al. |
| 2003/0078509 A1 | 4/2003 | Panescu |
| 2003/0216630 A1 | 11/2003 | Jersey-Willuhn et al. |
| 2004/0077942 A1 | 4/2004 | Hall et al. |
| 2004/0097806 A1 | 5/2004 | Hunter et al. |
| 2004/0243015 A1 | 12/2004 | Smith et al. |
| 2004/0254437 A1 | 12/2004 | Hauck et al. |
| 2005/0033136 A1 | 2/2005 | Govari et al. |
| 2005/0038337 A1 | 2/2005 | Edwards |
| 2005/0054918 A1 | 3/2005 | Sra |
| 2005/0107834 A1 | 5/2005 | Freeman et al. |
| 2005/0154282 A1 | 7/2005 | Li et al. |
| 2005/0288599 A1 | 12/2005 | MacAdam et al. |
| 2006/0085049 A1 | 4/2006 | Cory et al. |
| 2006/0116575 A1 | 6/2006 | Willis |
| 2006/0122526 A1 | 6/2006 | Berenfeld et al. |
| 2006/0173251 A1 | 8/2006 | Govari et al. |
| 2006/0178587 A1 | 8/2006 | Khoury |
| 2006/0241401 A1 | 10/2006 | Govari et al. |
| 2007/0016007 A1 | 1/2007 | Govari et al. |
| 2007/0038078 A1 | 2/2007 | Osadchy |
| 2007/0049821 A1 | 3/2007 | Willis |
| 2007/0083194 A1 | 4/2007 | Kunis et al. |
| 2007/0197929 A1 | 8/2007 | Porath et al. |
| 2007/0265539 A1 | 11/2007 | Hastings et al. |
| 2007/0270703 A1 | 11/2007 | He et al. |
| 2007/0287902 A1 | 12/2007 | Fuimaono et al. |
| 2007/0299351 A1 | 12/2007 | Harlev et al. |
| 2007/0299352 A1 | 12/2007 | Harlev et al. |
| 2007/0299353 A1 | 12/2007 | Harlev et al. |
| 2008/0190438 A1 | 8/2008 | Harlev et al. |
| 2008/0221566 A1 | 9/2008 | Krishnan |
| 2008/0234588 A1 | 9/2008 | Feldman et al. |
| 2008/0249424 A1 | 10/2008 | Harlev et al. |
| 2009/0171274 A1 | 7/2009 | Harlev et al. |
| 2009/0177072 A1 | 7/2009 | Harlev et al. |
| 2009/0253976 A1 | 10/2009 | Harlev et al. |

(56) References Cited

U.S. PATENT DOCUMENTS

| | | |
|---|---|---|
| 2009/0299355 A1 | 12/2009 | Bencini et al. |
| 2010/0286551 A1 | 11/2010 | Harlev et al. |
| 2012/0271135 A1 | 10/2012 | Burke et al. |
| 2012/0277567 A1 | 11/2012 | Harlev et al. |
| 2013/0172715 A1 | 7/2013 | Just et al. |
| 2013/0274582 A1 | 10/2013 | Afonso et al. |
| 2013/0345538 A1 | 12/2013 | Harlev et al. |
| 2014/0018880 A1 | 1/2014 | Zarins et al. |
| 2014/0200442 A1 | 7/2014 | Harlev et al. |
| 2014/0238175 A1 | 8/2014 | Huszar et al. |
| 2014/0275921 A1 | 9/2014 | Harlev et al. |
| 2015/0223726 A1 | 8/2015 | Harlev |
| 2015/0342491 A1 | 12/2015 | Marecki et al. |
| 2015/0374252 A1 | 12/2015 | de la Rama et al. |
| 2017/0143227 A1 | 5/2017 | Marecki et al. |

FOREIGN PATENT DOCUMENTS

| | | |
|---|---|---|
| EP | 0779059 B1 | 6/1997 |
| EP | 1484026 A1 | 12/2004 |
| EP | 2265172 A2 | 12/2010 |
| EP | 2269505 B1 | 5/2012 |
| JP | H08511438 A | 12/1996 |
| JP | H11504541 A | 4/1999 |
| JP | 2002078694 A | 3/2002 |
| JP | 2011507656 A | 3/2011 |
| JP | 2014518654 A | 8/2014 |
| JP | 2016521180 A | 7/2016 |
| WO | WO9725917 A1 | 7/1997 |
| WO | 2008097767 A2 | 8/2008 |
| WO | 2009085108 A1 | 7/2009 |
| WO | 2009123819 A2 | 10/2009 |
| WO | 2013028998 A2 | 2/2013 |
| WO | 2014110579 A1 | 7/2014 |
| WO | 2015187386 A1 | 12/2015 |
| WO | 2015187430 A2 | 12/2015 |

OTHER PUBLICATIONS

Makela et al., "A Review of Cardiac Image Registration Methods", IEEE Transaction on Medical Imaging, 21 (9):1011-1021, 2002.
Malladi, R. et al., "A Geometric Approach to Segmentation and Analysis of 3D Medical Images", Mathematical Methods in Biomedical Image Analysis, Proceedings of the Workshop on, Jun. 21-22, 1996, pp. 244-252.
Mangan, Alan et al., "Partitioning 3D Surface Meshes Using Watershed Segmentation", IEEE Transactions on Visualization and Computer Graphics, 5(4):308-321, 1999.
Meininger et al., "Initial Experience with a Novel Focused Ultrasound Ablation System for Ring Ablation Outside the Pulmonary Vein", Journal of Interventional Cardiac Electrophysiology, 8:141-148, 2003.
Merrill, Daniel R. et al., "Electrical stimulation of excitable tissue: design of efficacious and safe protocols", Journal of Neuroscience Methods, 141:171-198, 2005.
Miller, "Editor's Forum—Application of Registration for Ablation: A Marriage of Technologies", Journal of Interventional Cardiac Electrophysiology, 11:87-89, 2004.
Nademanee et al., "A New Approach for Catheter Ablation of Atrial Fibrillation: Mapping of the Electrophysiologic Substrate", Journal of the American College of Cardiology, 43(11):2044-2053, 2004.
Non-Final Office Action in U.S. Appl. No. 11/451,908. dated Sep. 4, 2008, 12 pages.
Non-Final Office Action issued in U.S. Appl. No. 11/451,898 dated Sep. 25, 2008, 13 pages.
Noseworthy et al., "The Impact of Respiration on Left Atrial and Pulmonary Venous Anatomy: Implications for Image-Guided Intervention", Heart Rhythm, 2:1173-1178, 2005.
Pappone et al., "Robotic Magnetic Navigation for Atrial Fibrillation Ablation", Journal of the American College of Cardiology, 47(7): 1390-1400, 2006.
Paragios, "A Level Set Approach for Shape-Driven Segmentation and Tracking of the Left Ventricle", IEEE Transactions on Medical Imaging, 22(6):773-776, 2003.
Persson et al., "A Simple Mesh Generator in MATLAB", SIAM Review, 46(2):329-345, 2004.
Persson, "Mesh Generation for Implicit Geometries", Massachusetts Institute of Technology—Thesis, Feb. 5, 2006.
Pham, Dzung, et al., "Current Methods in Medical Image Segmentation", Annu. Rev. Biomed, Eng., 02:315-337, 2000.
Rao et al., "Novel Noncontact Catheter System for Endocardial Electrical and Anatomical Imaging", Annals of Biomedical Engineering, 32(4):573-584, 2004.
Reddy et al., "Use of a Diode Laser Balloon Ablation Catheter to Generate Circumferential Pulmonary Venous Lesions in an Open-Thoracotomy Caprine Model", PACE, 27:52-57, 2004.
Reddy et al., "Integration of Cardiac Meagnetic Resonance Imaging with Three-Dimentional Electroanatomic Mapping to Guide Left Ventricular Catheter Manipulation—Feasibility is a Porcine Modelof Healed Myocardial Infarction", Journal of the American College of Cardiology, 44(11):2202-2213, 2004.
Sanders et al., "Spectral Analysis identifies Sites of High-Frequency Activity Maintaining Atrial Fibrillation in Humans", Circulation, 112:789-797, 2005.
Sethian, "Level Set Methods and Fast Marching Methods: Evolving Interfaces in Computational Geometry, Fluid Mechanics, Computer Vision, and Materials Science", Department of Mathematics—University of California, Berkeley, Cambridge University Press, 1999.
Simon et al. "Electroanatomic Mapping of the Right Arm With a Right Atrial Basket Catheter and Three-Dimensional Intracardiac Echocardiography", PACE, 27: 318-326, 2004.
Smits et al., "Catheter-Based Intramyocarial Injection of Autologous Skeletal Myoblasts as a Primary Treatment of Ischemic Heart Failure", Journal of the American College of Cardiology, 42(12):2063-2069, 2003.
Solomon et al., "Real-Time Cardiac Catheter Navigation on Three-Dimensional CT Images", Journal of Interventional Cardiac Electrophysiology, 8:27-36, 2003.
Sra et al., "Registration of Three-Dimensional Left Atrial Computed Tomographic Images With Projection Images Obtained Using Fluoroscopy", Circulation, 112:3763-3768, 2005.
Sra, Jasbir et al, "Registration of 3D Computed Tomographic Images With Interventional Systems: Implications for Catheter Ablation of Atrial Fibrillation", J Intery Card Electrophysiol, 16:141-148, 2006.
Stevenson, "Radiofrequency Catheter Ablation of Ventricular Tachycardia After Myocardial Infarction", Circulation, 98:308-314, 1998.
Taccardi et al., "A New Intracavitary Probe for Detecting the Site of the Origin of Ectopic Ventricular Beats During One Cardiac Cycle", Circulation, 75(1):272-281, 1987.
Thal et al., "Novel Applications in Catheter Ablation", Journal of Interventional Cardiac Electrophysiology, 13:17-21, 2005.
Thiagalingam et al., "Noncontact Mapping of the Left Ventricle: Insights from Validation With Transmural Contact Mapping", PACE, 27:570-578, 2004.
Voth, "The Inverse Problem of Electrocardiography: Industrial Solutions and Simulations", BEM and NFSI Conference Proceedings, Minneapolis, MN, May 12-15, 2005, pp. 191-194.
Wittkampf et al., "LocaLisa: New Technique for Real-Time 3-Dimensional Localization of Regular Intracardiac Electrodes", Circulation, 99:1312-1317, 1999.
Written Opinion of the International Searching Authority issued in PCT/US208/13553, dated Feb. 5, 2009, 6 pages.
Yezzi, Anthony et al., "A Geometric Snake Model for Segmentation", IEEE Transactions on Medical Imaging, 16(2) Apr. 1997.
Written Opinion of International Searching Authority issued in PCT/US2009/061277, dated Apr. 8, 2010, 10 pages.
Adams et al., "Seeded Region Growing", IEEE Transactions on Pattern Analysis and Machine Intelligence, 16 (6):641-647, 1994.
Arthur, "Clinical Use of Intracardiac Impedance: Current Applications and Future Perspectives", PACE, vol. 24:500-506, Apr. 2001.

(56) References Cited

OTHER PUBLICATIONS

Authorized officer Carl H. Layno, International Search Report and the Written Opinion in PCT/US07/70854 dated Sep. 12, 2008, 15 pages.
Authorized officer Lee W. Young, International Search Report and the Written Opinion in PCT/US08/52385 dated Aug. 8, 2008, 11 pages.
Authorized officer, Blaine R. Copenheaver, International Search Report and the Written Opinion in PCT/US2009/061277 dated Apr. 8, 2010, 13 pages.
Baan, Jan et al., "Continuous Measurement of Left Ventricular Volume in Animals and Humans by Conductance Catheter", Circulation, 07(5):812-823, 1984.
Badics, "Real-Time Reconstruction of Endocardial Potential Maps in Non-Contact Cardiace Mapping", International Journal for computation and Mathematics in Electrical Engineering (COMPEL), vol. 28, No. 4, 2009.
Ben-Haim et al., "Nonfluoroscopic, in Vivo Navigation and Mapping Technology", Nature Medicine, 2(12):1393-1395, 1996.
Besl et al., "A Method for Registration of 3-D Shapes", IEEE Transaction on Pattern Analysis and Machine Intelligence, 14(2):239-256, 1992.
Blomstrom-Lundqvist et al., "ACC/AHA/ESC Guidelines for the Management of Patients with Supraventricular Arrhythmias—Executive Summary", Journal of the American College of Cardiology, 42(8):1493-1531, 2003.
Breithardt et al., "AHA Medical/Scientific Statement—Special Report: Standards for Analysis of Ventricular Late Potentials Using High-Resolution or Signal/Averaged Electrocardiography", Circulation, 83(4):1481-1488, 1991.
Brooks et al., "Electrical Imaging of the Heart", IEEE Signal Processing Magazine, pp. 24-42, 1997.
Caspi et al., "Stem Cell Research: Regenerating the Heart Using Human Embryonic Stem Cells—from Cell to Bedside", IMAJ 8:208-214, 2006.
Cheney et al, "Electrical Imedance Tomography," SIAM Review 41, pp. 85-101, 1999.
Communication pursuant to Article 94(3) EPC in European Application No. 07798369, dated Nov. 17, 2011, 5 pages.
De Groot et al., "Three-Dimensional Catheter Positioning During Radiofrequency Ablation in Patients: First Application of a Real-Time Position Management System", Journal of Cardiovascular Electrophysiology, 11:1183-1192, 2000.
Donahue et al., "Focal Modification of Electrical Conduction in the Heart by Viral Gene Transfer", Nature Medicine, 6 (12):1395-1398, 2000.
Dong et al., "Integrated Electroanatomic Mapping With Three-Dimensional Computed Tomographic Images for Real-Time Guided Ablations", Circulation 113:186-194, 2006.
Durrer et al., "Total Excitation of the Isolated Human Heart", Circulation, XL1:899-912, 1970.
Ector, Joris et al., "Cardiac Three-Dimensional Magnetic Resonance Imaging and Fluoroscopy Merging", Circulation, 112:3769-3776, 2005.
European Search Report issued in EP Application No. 12815179.2, dated Apr. 28, 2015, 6 pages.
Extended European Search Report issued in EP Application No. 09727423.7, dated May 15, 2012, 5 pages.
Friedman, "Catheter Cryoablation of Cardiac Arrhythmias", Current Opinion in Cardiology, 20:48-54, 2005.
Friedman, "Novel Mapping Techniques for Cardiac Electrophysiology", Heart, 87:575-582, 2002.
Geddes et al., "Criteria for the Selection of Materials for Implanted Electrodes," Annals of Biomedical Engineering 31:879-890, 2003.

Gepstein et al., "A Novel Method for Nonfluoroscopic Catheter-Based Electroanatomical Mapping of the Heart", Circulation 95:1611-1622, 1997.
Haug. E. J. et al.: Design Sensitivity Analysis of Structural Systems, Mathematics in Science and Engineering, vol. 177 (1986).
Huang, Yi-Chih et al., "Development of a Third Generation Intraventricular Impedance Imaging (Iii) System Evaluation of Hardware Design", Engineering in Medicine and Biology Society, Proceedings of the 19th Annual Internal Conference of the IEEE/EMBS, 6:2442-2444 Oct. 30-Nov. 2, 1997.
International Preliminary Report on Patentability issued in PCT/US2008/013553, dated Feb. 5, 2009, 6 pages.
International Preliminary Report on Patentability issued in PCT/US2008/052385, dated Aug. 8, 2008, 6 pages.
International Preliminary Report on Patentability issued in PCT/US2009/036099, dated Oct. 14, 2010, 20 pages.
International Search Report and Written Opinion issued in PCT/US2009/036099, dated Apr. 28, 2009, 21 pages.
International Search Report and Written Opinion issued in PCT/US2014/060137, dated Dec. 10, 2014, 11 pages.
International Search Report and Written Opinion issued in PCT/US2015/032753, dated Mar. 9, 2016, 17 pages.
Jain et al., "Cell Therapy Attenuates Deleterious Ventricular Remodeling and Improves Cardiac Performance after Myocardial Infarction", Circulation, 103:1920-1927, 2001.
Jalife, "Rotors and Spiral Waves in Atrial Fibrillation", Journal of Cardiovascular Electrophysiology, 14:776-780, 2003.
Jane et al., Alignment Methods for Averaging of High-Resolution Cardiac Signals: A Comparative Study of Performance, IEEE Transaction on Biomedical Engineering, 38(6):571-579, 1991.
Jia et al., "Electrophysiologic Endocardial Mapping from a Noncontact Nonexpandable Catheter: A Validation Study of a Geometry-Based Concept". Journal of Cardiovascular Electrophysiology, 11:1238-1251, 2000.
Kikuchi et al., "Targeted Modification of Atrial Electrophysiology by Homogeneous Transmural Artial Gene Transfer", Circulation, 111:264-270, 2005.
Kistler et al., "Validation of Three-Dimensional Cardiac Image integration: Use of Integrated CT Image into Electroanatomic Mapping System to Performa Catheter Ablation of Atrial Fibrillation", Journal of Cardiovascular Electrophysiology, 17:341-348, 2006.
Kuklik et al., The reconstruction, from a set of points, and analysis of the interior surface of the heart chamber, Physiological Measurement 25, pp. 617-627, 2004.
Kun, Stevan et al., "Conductance Volumetric Model of an Eccentrically Positioned Catheter within a Three-Compartment Ellipsoidal Ventricle", U, IEEE Transactions on Jun. 1993, 40(6); 589-592.
L. Piegi, W. Tiller: The NURBS Book, 2nd Edition, Springer (1997).
Laciar et al., "Improved Alignment Method for Noisy High-Resolution ECG and Holter Records Using Multiscale Cross-Correlation", IEEE Transactions on Biomedical Engineering, 50(3):344-353, 2003.
Liu et al., "Endocardial Potential Mapping from a Noncontact Nonexpandable Catheter: A Feasibility Study", Annals of Biomedical Engineering, 26:994-1009, 1998.
International Preliminary Report on Patentability issued in PCT/US2015/032004, dated Dec. 6, 2016, 7 pages.
International Preliminary Report on Patentability issued in PCT/US2015/032753, dated Dec. 6, 2016, 10 pages.
International Preliminary Report on Patentability issued in PCT/US2014/060137, dated Apr. 28, 2016, 9 pages.
International Search Report and Written Opinion issued in PCT/US2015/032004, dated Sep. 4, 2015, 8 pages.

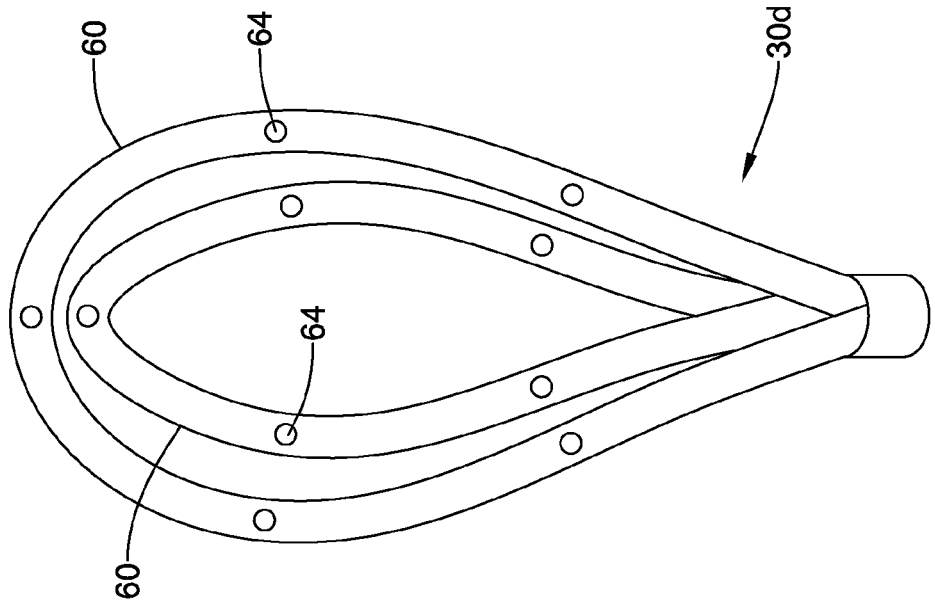
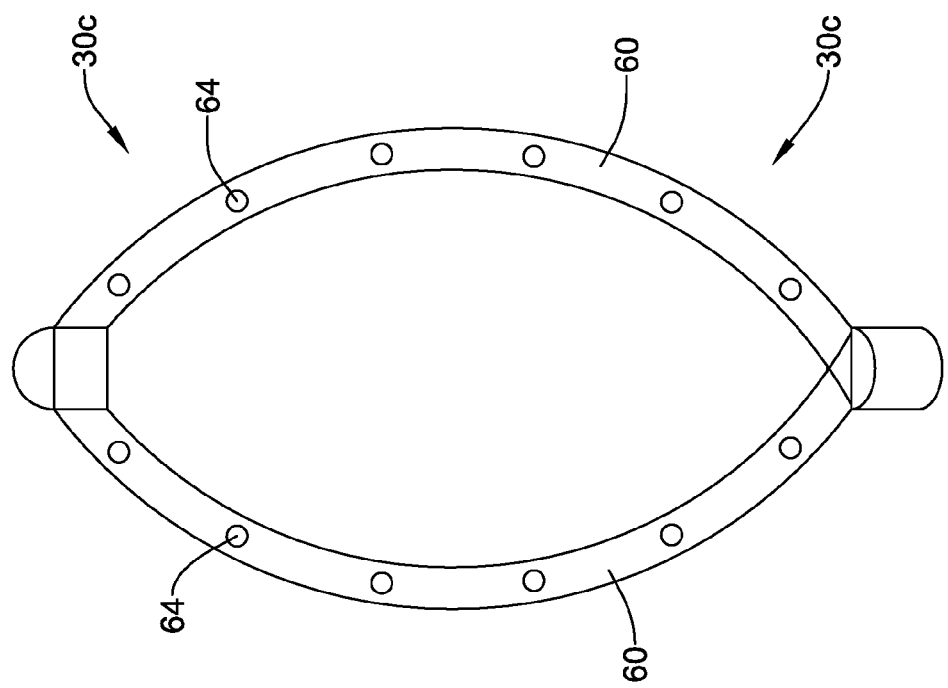

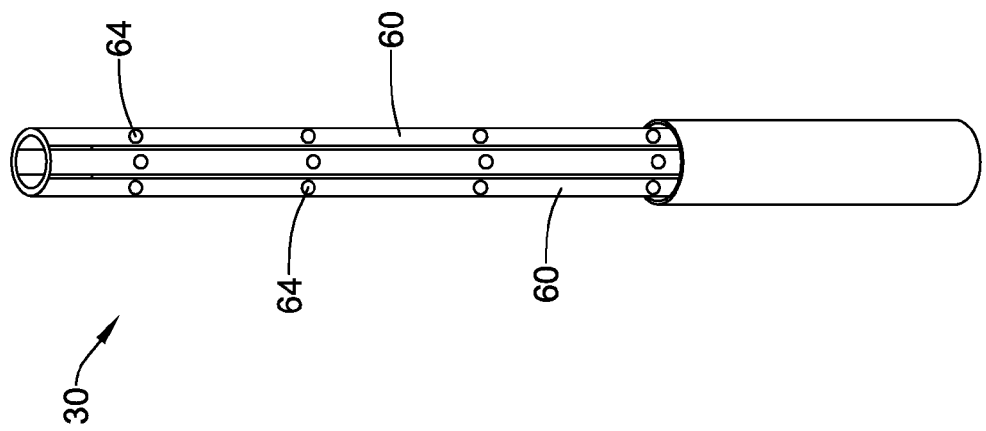

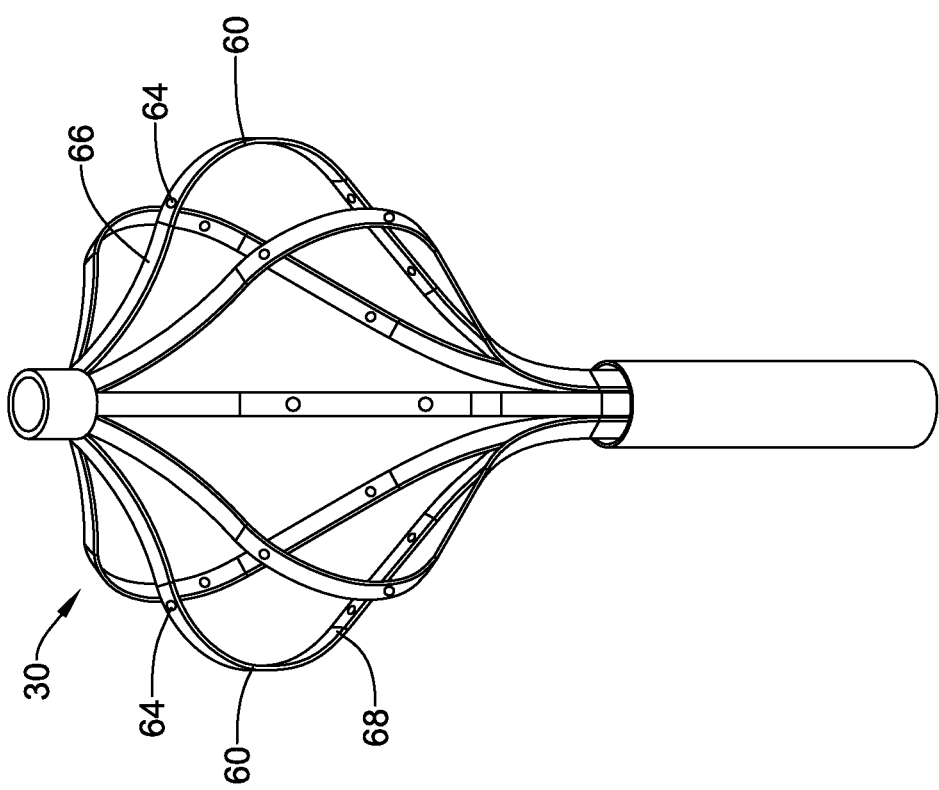

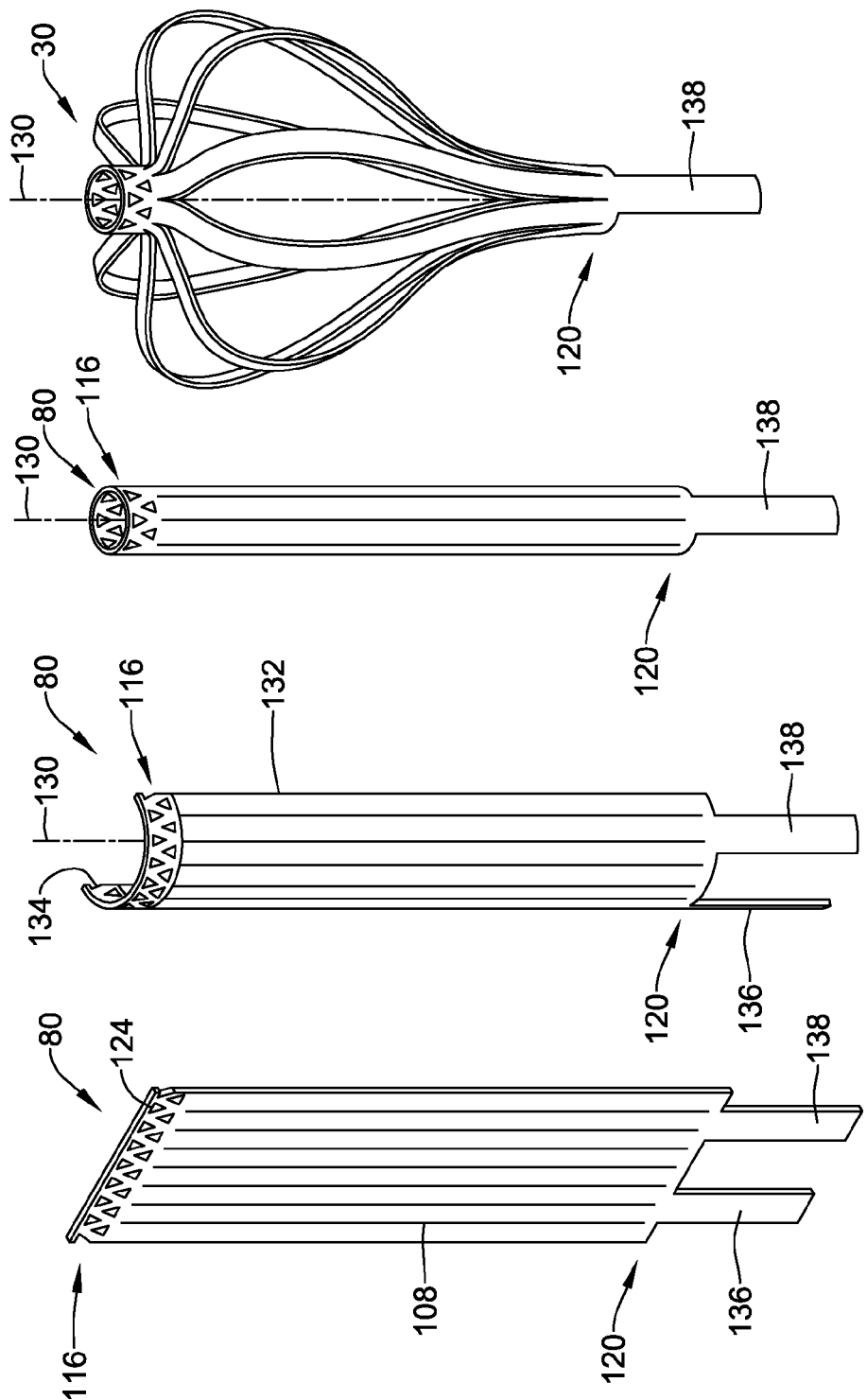

ELECTRODE ASSEMBLY

CROSS-REFERENCE TO RELATED APPLICATIONS

This application claims priority under 35 U.S.C. §119 to U.S. Provisional Application Ser. No. 62/007,716, filed Jun. 4, 2014, the entirety of which is incorporated herein by reference.

TECHNICAL FIELD

The present disclosure generally relates to catheters and electrode assemblies for use in cardiac procedures and more particularly, to an electrode assembly that may be utilized in a cardiac mapping procedure.

BACKGROUND

Mapping the electrical activity of the heart is a critical component for the diagnosis and treatment of heart disease. Many advanced therapies (such as ablation for the treatment of arrhythmias) require detailed electroanatomic mapping. Currently, mapping is performed in an electrophysiology (EP) lab, during which mapping catheters are inserted into the heart and carefully moved to various locations around the heart to map and identify the origins of the arrhythmia. Once the origin of the arrhythmia is identified, the specific tissue may be destroyed by ablation.

SUMMARY

The present disclosure generally relates to catheter and electrode assemblies for use in cardiac procedures and more particularly, to an electrode assembly that may be utilized in a cardiac mapping procedure.

In one example, a catheter includes: an elongate catheter body extending from a proximal end to a distal end; and an expandable electrode assembly disposed at the distal end of the catheter body, the electrode assembly configured to transition from a collapsed configuration to an expanded configuration and comprising at least one flexible member having an outer surface and an inner surface, wherein the at least one flexible member comprises a first electrode disposed on the outer surface of the flexible member and a second electrode disposed on the inner surface of the flexible member.

In addition or alternatively to any one or more of the above, and in another example, the first and second electrodes are configured to form a bipolar electrode pair.

In addition or alternatively to any one or more of the above, and in another example, the first electrode is located directly opposite the second electrode.

In addition or alternatively to any one or more of the above, and in another example, the first electrode is offset from the second electrode.

In addition or alternatively to any one or more of the above, and in another example, the flexible member comprises at least one flexible printed circuit.

In addition or alternatively to any one or more of the above, and in another example, the flexible member comprises a single, dual sided flexible printed circuit wherein the first electrode is formed on an outer surface of the flexible printed circuit and the second electrodes is formed on an inner surface of the flexible printed circuit.

In addition or alternatively to any one or more of the above, and in another example, the flexible member comprises a first flexible printed circuit defining the first electrode formed on an upper surface of a substrate and a second flexible printed circuit defining the second electrode formed on a lower surface of the substrate.

In addition or alternatively to any one or more of the above, and in another example, a distance between the first electrode and the second electrode is less than about 0.5 mm.

In addition or alternatively to any one or more of the above, and in another example, the flexible member comprises multiple bipolar electrode pairs defined by a first electrode disposed on the outer surface of the flexible member and a second electrode disposed on the inner surface of the flexible member.

In addition or alternatively to any one or more of the above, and in another example, further comprising two or more flexible members, each of the two or more flexible members comprising at least a first electrode disposed on the outer surface of the flexible member and at least a second electrode disposed on the inner surface of the flexible member.

In addition or alternatively to any one or more of the above, and in another example, wherein the first and second electrodes form a bipolar electrode pair across the outer and inner surface of the flexible member.

In another example, a method of forming a flexible electrode assembly includes: forming a flexible electrode assembly comprising at least one flexible member having an outer surface and an inner surface, wherein the at least one flexible member comprises a first electrode disposed on the outer surface of the flexible member and a second electrode disposed on the inner surface of the flexible member and wherein the flexible electrode assembly is configured to transition from a collapsed configuration to an expanded configuration; and coupling the flexible electrode assembly to a distal end of an elongate catheter body.

In addition or alternatively to any one or more of the above, and in another example, the method further includes: forming a flexible layered sheet comprising at least one flexible printed circuit defining a first electrode on an outer surface of the flexible layered sheet and a second electrode on an inner surface of the flexible layered sheet; separating the flexible layered sheet into two or more flexible members, each flexible member having a first electrode located on an outer surface and a second electrode located on an inner surface; and forming an expandable electrode assembly from at least one of the flexible members.

In addition or alternatively to any one or more of the above, and in another example, the method further includes forming an expandable electrode assembly from two or more flexible members by joining the two or more flexible members together at a first end of each of the two or more flexible members.

In addition or alternatively to any one or more of the above, and in another example, the method further includes joining the two or more flexible members together at a second end of each of the two or more flexible members.

In another example, a catheter includes an elongate catheter body extending from a proximal end to a distal end; and an expandable electrode assembly disposed at the distal end of the catheter body, the electrode assembly configured to transition from a collapsed configuration to an expanded configuration and comprising at least one flexible member having an outer surface and an inner surface, wherein the at least one flexible member comprises a first electrode disposed on the outer surface of the flexible member and a second electrode disposed on the inner surface of the flexible member.

In addition or alternatively to any one or more of the above, and in another example, the first and second electrodes are configured to form a bipolar electrode pair.

In addition or alternatively to any one or more of the above, and in another example, the first electrode is located directly opposite the second electrode.

In addition or alternatively to any one or more of the above, and in another example, the first electrode is offset from the second electrode.

In addition or alternatively to any one or more of the above, and in another example, the catheter further includes two or more flexible members, each of the two or more flexible members comprising at least a first electrode disposed on the outer surface of the flexible member and at least a second electrode disposed on the inner surface of the flexible member.

In addition or alternatively to any one or more of the above, and in another example, the flexible member comprises at least one flexible printed circuit.

In addition or alternatively to any one or more of the above, and in another example, the flexible member comprises a single, dual sided flexible printed circuit wherein the first electrode is formed on an outer surface of the flexible printed circuit and the second electrodes is formed on an inner surface of the flexible printed circuit.

In addition or alternatively to any one or more of the above, and in another example, the flexible member comprises a first flexible printed circuit defining the first electrode formed on an upper surface of a substrate and a second flexible printed circuit defining the second electrode formed on a lower surface of the substrate.

In addition or alternatively to any one or more of the above, and in another example, a distance between the first electrode and the second electrode is less than about 0.5 mm.

In addition or alternatively to any one or more of the above, and in another example, the flexible member comprises multiple bipolar electrode pairs defined by a first electrode disposed on the outer surface of a flexible member and a second electrode disposed on the inner surface each of the flexible member.

In another example, a catheter includes: an elongate catheter body extending from a proximal end to a distal end; and an expandable electrode assembly disposed at the distal end of the catheter body, the electrode assembly configured to transition from a collapsed configuration to an expanded configuration and comprising two or more flexible splines having an outer surface and an inner surface, wherein at least one of the two or more flexible splines comprises at least a first electrode disposed on the outer surface of the flexible spline and at least a second electrode disposed on the inner surface of the flexible spline.

In addition or alternatively to any one or more of the above, and in another example, the first and second electrodes are configured to form a bipolar electrode pair.

In addition or alternatively to any one or more of the above, and in another example, the first electrode is located directly opposite the second electrode.

In addition or alternatively to any one or more of the above, and in another example, the first electrode is offset from the second electrode.

In addition or alternatively to any one or more of the above, and in another example, each of the two or more splines comprises multiple bipolar electrode pairs defined by a first electrode disposed on the outer surface of a flexible spline and a second electrode disposed on the inner surface of the flexible spline.

In addition or alternatively to any one or more of the above, and in another example, each of the two or more flexible splines comprises at least one flexible printed circuit.

In addition or alternatively to any one or more of the above, and in another example, the at least one flexible circuit is a single, dual sided flexible printed circuit having a first electrode is formed on an upper surface of the flexible printed circuit and a second electrode formed on a lower surface of the flexible printed circuit.

In addition or alternatively to any one or more of the above, and in another example, each of the two or more flexible splines comprises a first flexible printed circuit defining a first electrode formed on an upper surface of a substrate and a second flexible printed circuit defining a second electrode formed on a lower surface of the substrate.

In yet another example, a method of forming a flexible electrode assembly includes: forming a flexible electrode assembly comprising at least one flexible member having an outer surface and an inner surface, wherein the at least one flexible member comprises a first electrode disposed on the outer surface of the flexible member and a second electrode disposed on the inner surface of the flexible member and wherein the flexible electrode assembly is configured to transition from a collapsed configuration to an expanded configuration; and coupling the flexible electrode assembly to a distal end of an elongate catheter body.

In addition or alternatively to any one or more of the above, and in another example, the method further includes forming a flexible layered sheet comprising at least one flexible printed circuit defining a first electrode on an outer surface of the flexible layered sheet and a second electrode on an inner surface of the flexible layered sheet; separating the flexible layered sheet into two or more flexible members, each flexible member having a first electrode located on an outer surface and a second electrode located on an inner surface; and forming the expandable electrode assembly from at least one of the flexible members.

In addition or alternatively to any one or more of the above, and in another example, the method further includes forming an expandable electrode assembly from two or more flexible members by joining the two or more flexible members together at least at a first end of each of the two or more flexible member.

In still another example, a method of forming a flexible electrode assembly is disclosed. The method includes: forming a first flexible printed circuit comprising one or more electrodes on an upper surface of a substrate and forming a second flexible printed circuit comprising one or more electrodes on a lower surface of the substrate to produce a flexible layered sheet; separating the flexible layered sheet into two or more splines extending longitudinally from a proximal end of the flexible layered sheet to a distal end of the flexible layered sheet, wherein the two or more splines are fully separated from one another such that they are not connected and wherein each of the two or more splines comprises at least one bipolar electrode pair defined by a first electrode from the first flexible printed circuit disposed on the upper surface of the substrate and a second electrode from the second flexible printed circuit disposed on the lower surface of the substrate, each electrode located on opposite sides of each of the two or more splines; mechanically joining the fully separated two or more flexible splines together to form an expandable electrode assembly.

In addition or alternatively to any one or more of the above, the substrate comprises Nitinol.

In addition or alternatively to any one or more of the above, the step of separating the flexible layered sheet into two or more splines comprises laser cutting the flexible layered sheet into two or more splines.

In addition or alternatively to any one or more of the above, the step of separating the flexible layered sheet into two or more splines comprises die cutting the flexible layered sheet into two or more splines.

In addition or alternatively to any one or more of the above, the method further includes securing a second end of the first spline and a second end of the second spline to a distal end of a catheter body.

In addition or alternatively to any one or more of the above, wherein the fully separated splines are mechanically joined together by inserting their respective distal ends into corresponding slots provided in a distal cap.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description of various embodiments in connection with the accompanying drawings, in which:

FIGS. 3A-3G are schematic views of exemplary expandable electrode assemblies;

FIG. 4A is an isometric view of an expandable electrode assembly shown in a collapsed configuration;

FIG. 4B is an isometric view of the expandable electrode assembly of FIG. 4A shown in an expanded configuration;

FIGS. 9A-9D provide a stepwise illustration of a method of constructing the expandable electrode assembly from a multi-layered flexible sheet including at least one flexible printed circuit.

Figure 1:
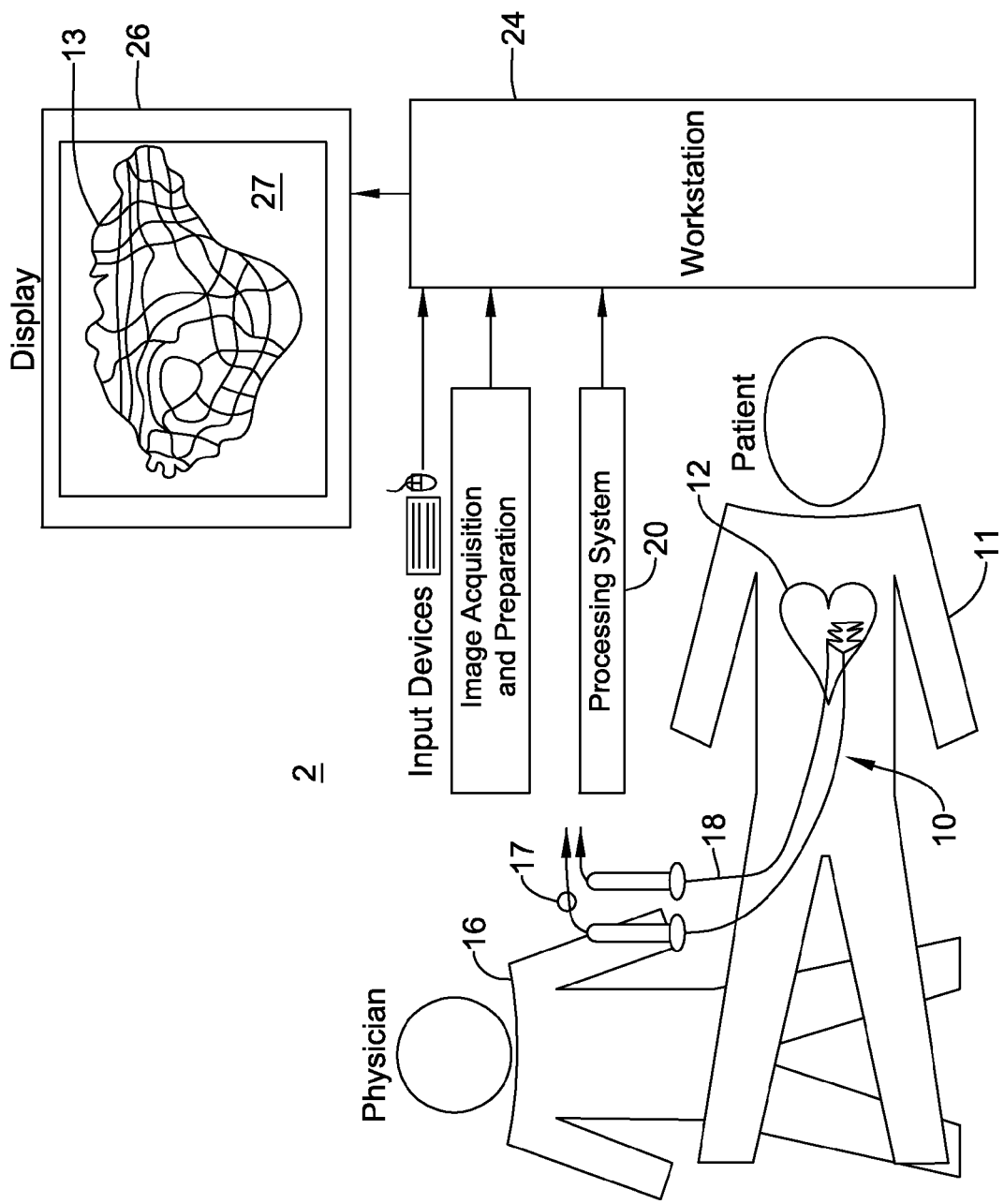
FIG. 1 is a schematic diagram showing a catheter in the context of a system.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Mapping the electrophysiology of heart rhythm disorders often involves the introduction of a constellation catheter or other mapping/sensing device having a plurality of electrodes and/or sensors (e.g., CONSTELLATION®, commercially available from Boston Scientific) into a cardiac chamber. The sensors detect the electric activity of the heart at sensor locations. It may be desirable to have the electric activity processed into electrogram signals that accurately represent cellular excitation through cardiac tissue relative to the sensor locations. A processing system may then analyze and output the signal to a display device. Further, the processing system may output the signal as an activation or vector field map. The physician may use the activation or vector field map to perform a diagnostic procedure.

FIG. 1 is a high level, schematic view of an overall system 2 that includes a physician, a patient, catheters, including a mapping catheter 10, and related electrophysiology equipment located within an operating room. A physician 16 introduces the catheter 10 into the vasculature of the patient 11 at the patient's leg and advances it along a blood vessel ultimately, entering the patient's heart 12. As will be described in greater detail herein, the catheter 10 may include an electrode assembly having multiple sensing electrodes for sensing the electrical activity of the heart. Other catheters that may be used in the procedure are represented by companion catheter 18. Each catheter 10, 18 is coupled to a processing system 20 using appropriate catheter cabling typified by connection cable 17. If the companion catheter 18 is an ablation catheter, then processing system 20 also forms an interface to an RF ablation unit (not illustrated).

Processing system 20 may include dedicated circuitry (e.g., discrete logic elements and one or more microcontrollers; a memory or one or more memory units, application-specific integrated circuits (ASICs); and/or specially configured programmable devices, such as, for example, programmable logic devices (PLDs) or field programmable gate arrays (FPGAs)) for receiving and/or processing the acquired activation signals. In at least some embodiments, processing system 20 includes a general purpose microprocessor and/or a specialized microprocessor (e.g., a digital signal processor, or DSP, which may be optimized for processing activation signals) that executes instructions to receive, analyze and display information associated with the received activation signals. In such implementations, processing system 20 can include program instructions, which when executed, perform part of the signal processing. Program instructions can include, for example, firmware, microcode or application code that is executed by microprocessors or microcontrollers. In addition, the processing system 20 may include suitable signal conditioning circuitry including signal amplifiers, rectifiers, filters, etc. for improving the quality of the incoming activation signal. The above-mentioned implementations are merely exemplary. A variety of processing systems 20 are contemplated.

In some embodiments, processing system 20 may be configured to measure the electrical activity in the myocardial tissue adjacent to one or more electrodes located on the electrode assembly. For example, in some embodiments, processing system 20 may be configured to detect electrical activity associated with a dominant rotor or divergent activation pattern in the anatomical feature being mapped. Dominant rotors and/or divergent activation patterns may have a role in the initiation and maintenance of atrial fibrillation, and ablation of the rotor path, rotor core, and/or divergent foci may be effective in terminating the atrial fibrillation. In either situation, processing system 20 processes the sensed activation signals to generate a display of relevant characteristics, such as an isochronal map, activation time map, action potential duration (APD) map, a vector field map, a contour map, a reliability map, an electrogram, a cardiac action potential, and/or the like. The relevant characteristics may be used by the physician to identify a site suitable for ablation therapy.

In use, the physician looks at a computer display 26. Present on the display 26 is a substantial amount of information. A large window presents an image of the heart chamber 13 along with an image of the catheter 10. The physician will manipulate and control the catheter 10 based in part on the images and other data presented on the display 26. The representation of the heart chamber 13 may use color, wire frame, or other techniques to depict the structure of the heart chamber 13 and to simultaneously portray electrical activity of the patient's heart. In some cases, it may be useful to display chamber geometry, catheter location, and electrical activity in an integrated fashion on the display 26. In use, the physician will observe the display 26 and interact with the workstation 24 and the catheters 10 and 18, to direct a medical procedure such as, for example, a cardiac mapping procedure.

Figure 2A:
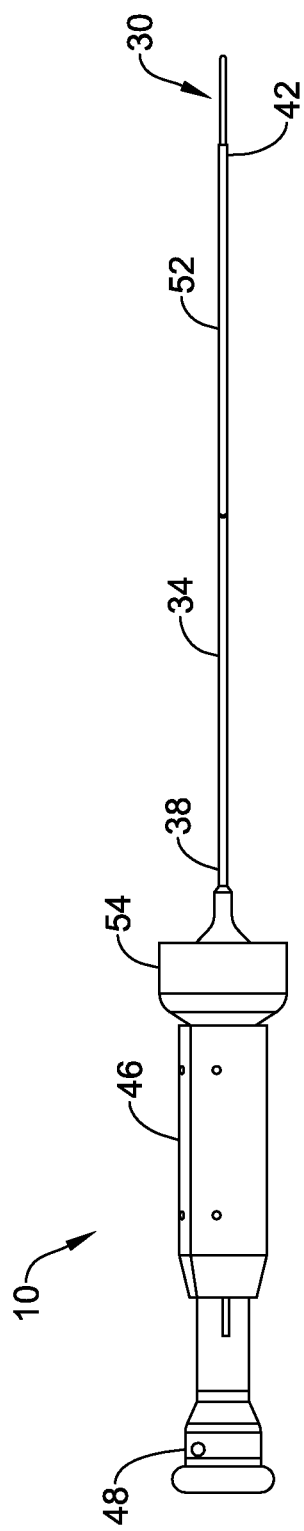
FIGS. 2A-2B are schematic views of an exemplary catheter that may be utilized in the system shown in FIG. 1.
Figure 2B:
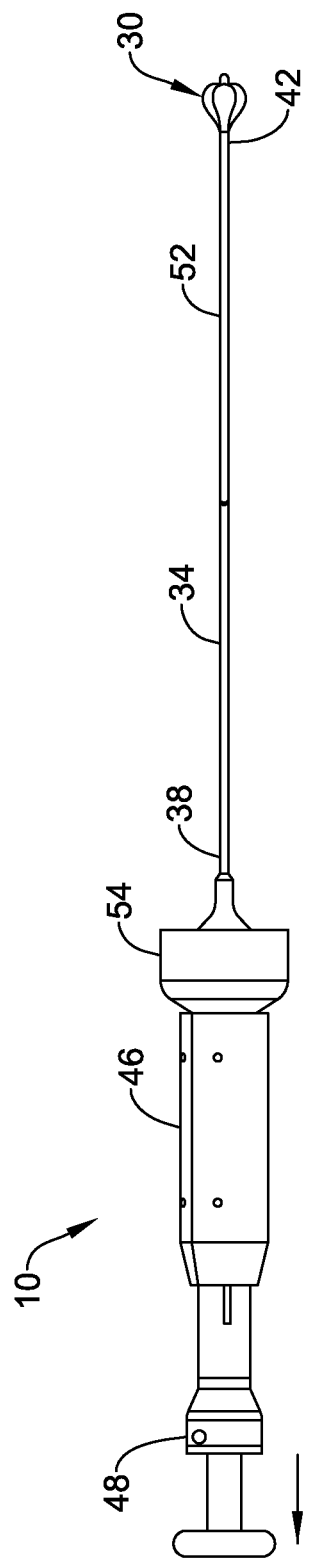
Figure 3B:
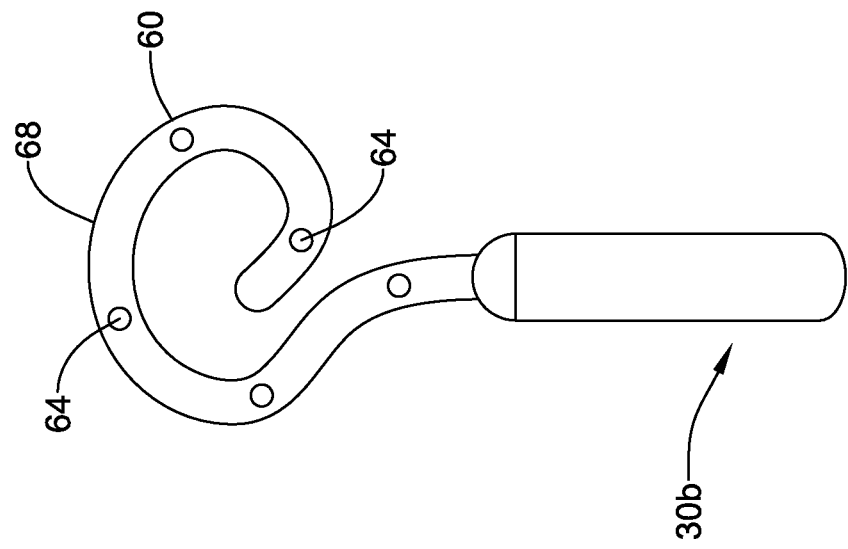
Figure 3A:
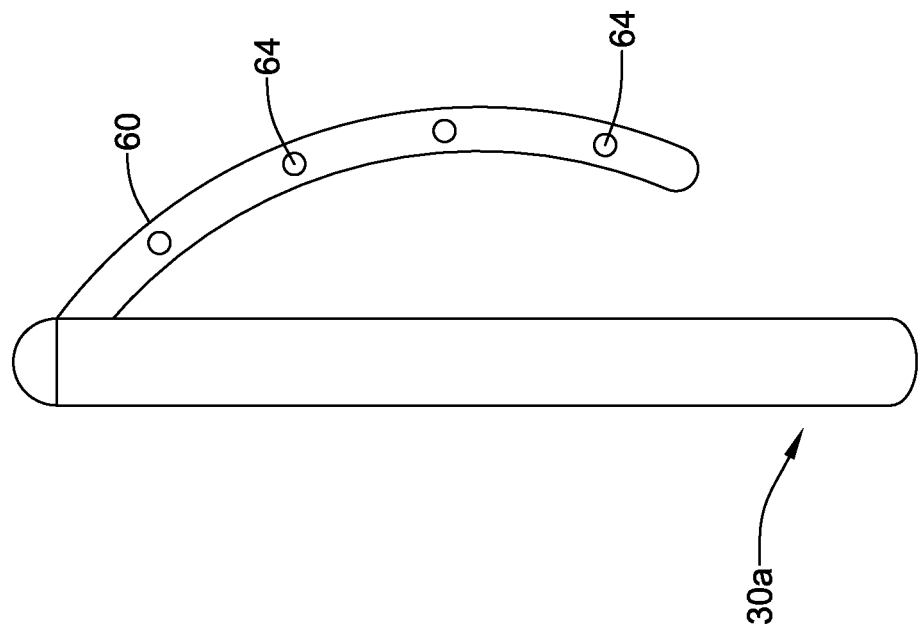
Figure 3F:
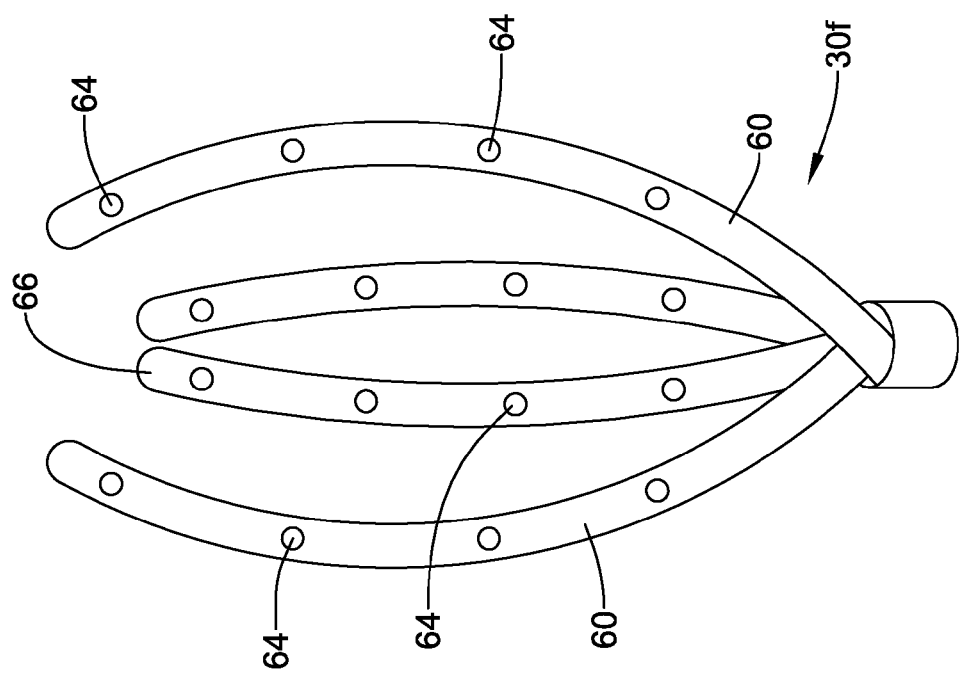
Figure 3E:
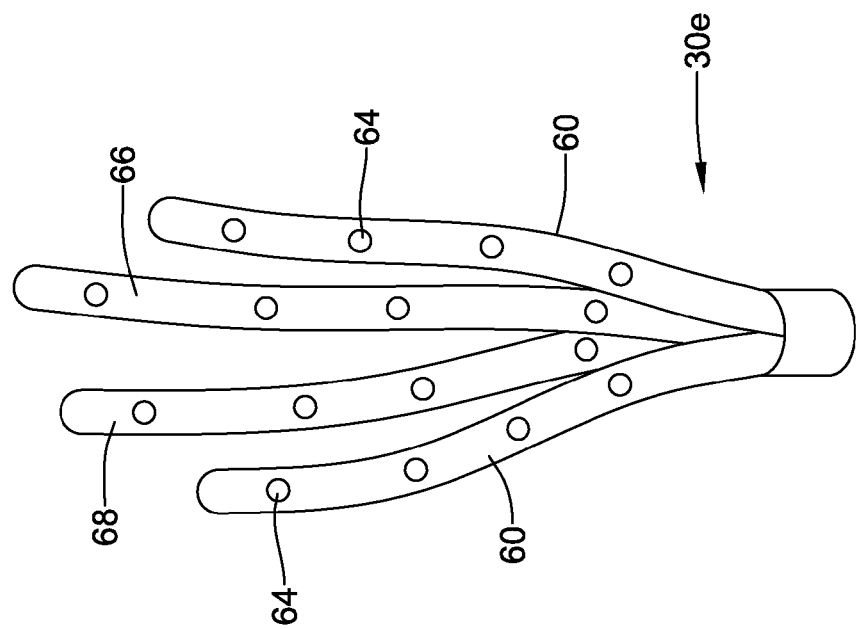
Figure 3G:
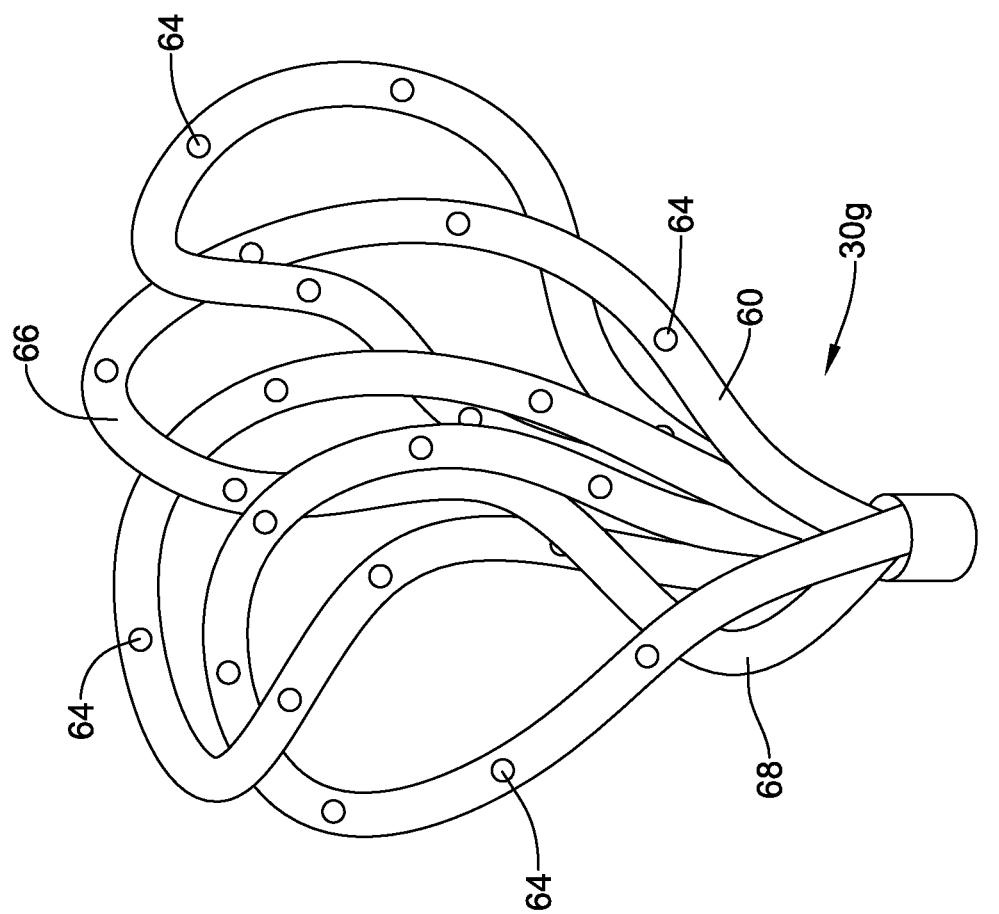

FIGS. 2A and 2B are schematic views of an exemplary intravascular catheter 10 that may be utilized in the context of the system 2 shown in FIG. 1. The catheter 10 may be deployed at a target location within a patient's heart. The catheter 10 may be used to map electro-anatomical characteristics of the heart and/or to locate and position other catheters within the heart. Electrode stability and the known spatial geometry of the electrodes may improve the accuracy of the mapping device. In some cases, the catheter 10 may include an expandable electrode assembly 30 including one or more electrodes that may be used for cardiac mapping or diagnosis, ablation and/or other therapies involving the application of energy to a patient's heart. The expandable one or more electrodes may be located on the inner and/or outer surfaces of at least one flexible member forming the expandable electrode assembly 30.

As shown in FIGS. 2A and 2B, the catheter 10 includes an elongate catheter body 34 extending from a proximal end 38 to a distal end 42. In addition, the catheter body 34 may include a lumen (not shown) extending there through, but this is not required in all embodiments. The catheter body 34 may have sufficient flexibility so as to navigate the tortuous pathways of a patient's vasculature system. The catheter 10 can include a handle assembly 46 coupled to the proximal end 38 of the catheter body 34. A physician may manipulate the handle assembly 46 to deliver, steer, rotate, deploy and/or deflect the catheter 10 when performing a medical procedure.

In some cases, the handle assembly 46 may include a first actuation mechanism 48 that may be manipulated to transition the expandable electrode assembly 30 from a collapsed configuration (shown in FIG. 2A) suitable for delivery of the catheter 10 to a target location within a patient's body (e.g. the heart) and an expanded configuration (shown in FIG. 2B) suitable for use in a diagnostic procedure and/or delivery of a therapy. In some cases, the actuation mechanism 48 may include a pull wire that may be coupled to the expandable electrode assembly 30 that, when actuated in a proximal direction as indicated by the arrow shown in FIG. 2B, causes the expandable electrode assembly 30 to transition from the collapsed configuration to the expanded configuration. In other cases, the actuation mechanism 48 may include a retractable sheath that, when retracted in a proximal direction as indicated by the arrow shown in FIG. 2B, may permit the expandable electrode assembly 30 to self-expand from the collapsed configuration to the expanded configuration. These are just some examples of exemplary actuation mechanisms that may be utilized to facilitate expansion of the expandable electrode assembly 30 when the catheter 10 is in use. In some cases, the catheter body 34 may include a deflectable distal portion 52 that a physician may manipulate using a second actuation mechanism 54 provided in the handle assembly 46 to position the electrode assembly 30 nearer or adjacent to tissue of interest.

As discussed herein, the expandable electrode assembly 30 may include one or more electrodes that may be used for cardiac mapping or diagnosis, ablation and/or other therapies. In use, the expandable electrode assembly 30 may be expanded and used to position the one or more electrodes adjacent and/or in contact with the target tissue of interest to measure an electrical signal. The expandable electrode assembly 30 may include at least one flexible member or spline on which the one or more electrodes may be located. In some cases, the expandable electrode assembly may include two or more flexible members as the size and geometry of the expandable electrode assembly 30 may permit. For example, the expandable electrode assembly may include four, five, six, seven, and in some cases as many as eight flexible members, but not limited to this. In some cases, the size, geometry and number of flexible members or splines may be dependent the location of the body in which the device is to be deployed to investigate the target tissue of interest. One or more electrodes 64 may be disposed on at least one of the flexible members forming the expandable electrode assembly 30. The electrodes 64 may be located on an inner surface, an outer surface or both the inner and outer surfaces of the at least one flexible member. In some cases, at least a first electrode 64 is located on an outer surface and at least a second electrode 64 is located on an inner surface of a flexible member. In many cases, the at least one flexible member 60 is substantially planar or flat. FIGS. 3A-3G are schematic views of exemplary expandable electrode assemblies 30a-30g including at least one flexible member 60 that may be used to support a plurality of electrodes 64 as described herein according to the various embodiments.

Figure 4C:
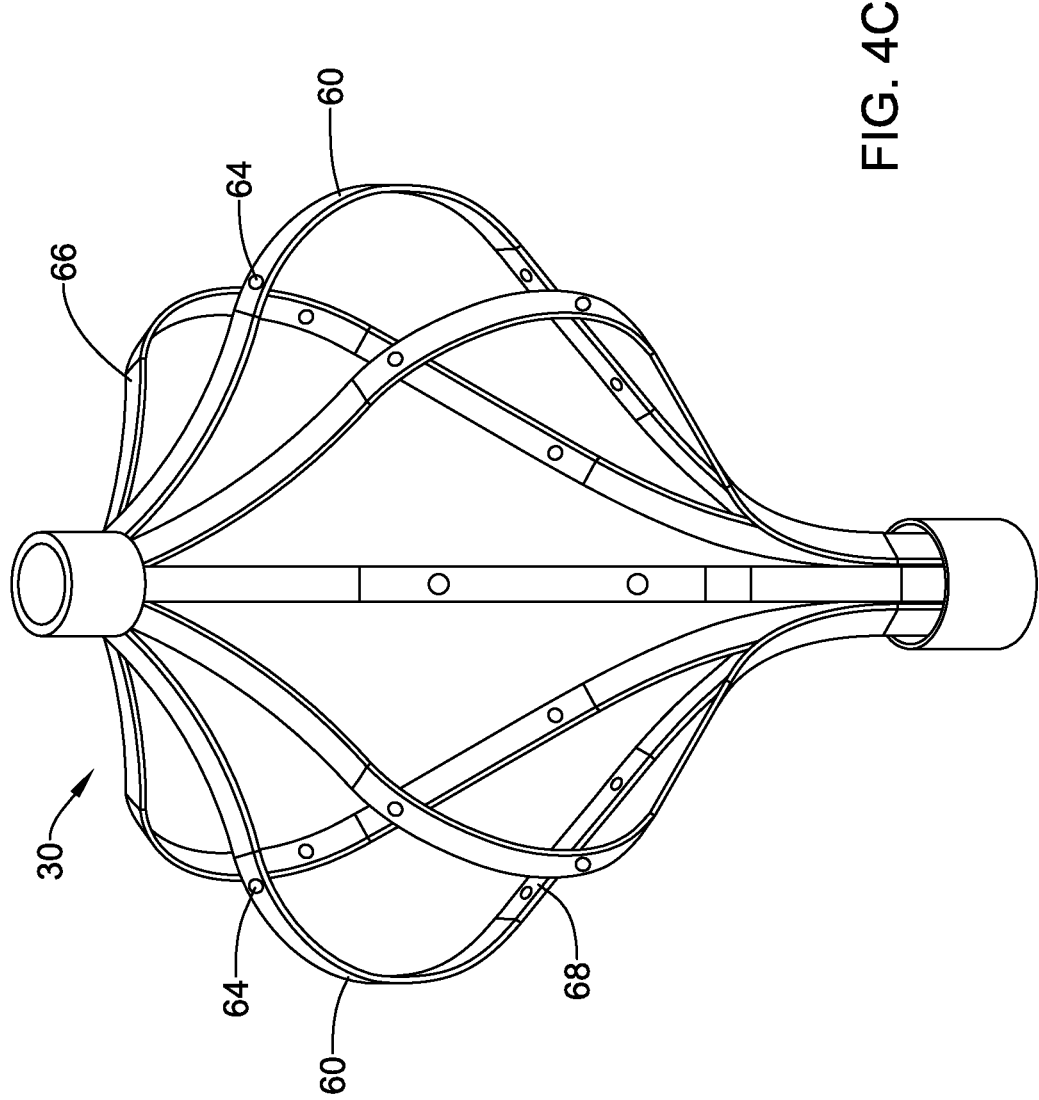
FIG. 4C is a close-up, isometric view of the expandable electrode assembly of FIG. 4B in the expanded configuration.
Figure 4D:
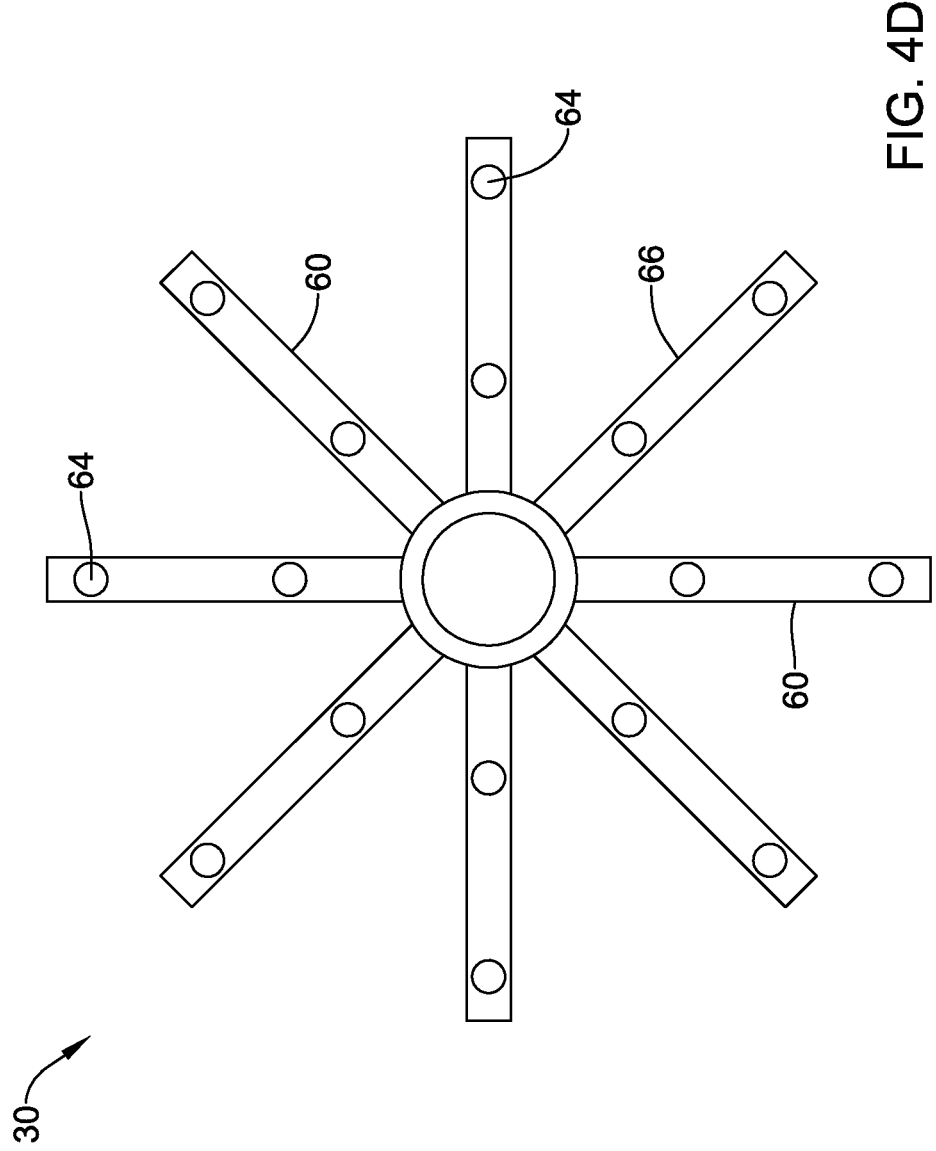
FIG. 4D is a top plan view of the expandable electrode assembly shown in FIGS. 4B and 4C in the expanded configuration.

FIGS. 4A-4D show different views of an exemplary expandable electrode assembly 30 that may be used to support a plurality of electrodes. As shown in FIGS. 4A and 4B, the expandable electrode assembly 30 is capable of being transitioned from a generally collapsed configuration (FIG. 4A) suitable for delivery of the catheter 10 and the electrode assembly 30 to a target location within the patient's heart and an expanded configuration (FIG. 4B) suitable for use in a desired cardiac procedure such as, for example, a cardiac mapping or ablation procedure.

As shown in FIGS. 4A and 4B, the expandable electrode assembly 30 may include two or more flexible members or splines 60 which may be capable of being flexed outwardly and away from a longitudinal axis of the electrode assembly 30. In some cases, as discussed herein, an actuation mechanism may be utilized to transition the electrode assembly 30 including the two or more flexible splines 60 from the collapsed configuration (FIG. 4A) to the expanded configuration (FIG. 4B). In other cases, the flexible splines 60 may incorporate a shape memory material that may facilitate self-expansion of the flexible splines 60 and consequently, the electrode assembly 30, from the collapsed configuration to the expanded configuration. The flexible splines 60 may be relatively stiff such that the electrode assembly 30 may be expanded into a set of known, reproducible shapes capable of retaining a known spatial geometry when in use which, in some cases, may be aided by the incorporation of a shape-memory material or other stiff polymeric material such as, for example, a polyimide or PEEK into the flexible splines 60. Alternatively, depending upon the desired application, the flexible splines 60 may be fabricated such that they are somewhat compliant so as to conform to a surface of a patient's heart when placed into intimate contact with the patient's heart. In addition, in some cases, the flexible members or splines 60 may be fabricated such that they are substantially planar or flat.

The expandable electrode assembly 30 may include a number of electrodes 64 located on each of the flexible splines 60 forming an electrode array. In many cases, the electrodes 64 may be sensing electrodes. In addition, the electrode assembly 30 may include at least some current injection locator electrodes. The electrode assembly 30 may also include a tip electrode which may be used for cardiac stimulation, ablation or as a locator electrode.

Each electrode 64 may be electrically connected to the cabling in the handle assembly 46. In some cases, the signal from each individual electrode 64 may be independently available at the processing system 20 (FIG. 1). This may be achieved by passing a conductor for each electrode through the connection cable 17 (FIG. 1).

The number of electrodes 64 distributed throughout the electrode assembly 30 and the stability of the shape of electrode assembly 30, when expanded, may affect the overall performance of the mapping system. In some cases, the electrodes 64 may have a uniform and symmetrical distribution throughout the expandable electrode assembly 30. In other cases, the electrodes 64 may have an asymmetrical distribution throughout the expandable electrode assembly 30 which may be advantageous for non-contact cardiac mapping procedures. An electrode assembly 30 having an asymmetrical distribution of electrodes 64 throughout the expandable electrode assembly 30 may also be useful for contact mapping.

The electrodes 64 may be located on the outer surfaces 66 of each of the splines 60, the inner surfaces 68 of each of the splines 60, or both the outer and inner surfaces 66, 68 of each of the flexible splines 60 as shown in FIGS. 4B and 4C. In some cases, up to sixty-four sensing electrodes 64 may be distributed over and along the various splines 60 including both the outer and inner surfaces 66, 68 of the splines 60. Depending upon the application, the electrode assembly 30 may include fewer or greater than sixty-four electrodes.

In many cases, the electrodes 64 may form at least one bipolar electrode pair. In some cases, the electrodes 64 may form multiple bipolar electrode pairs. The bipolar electrode pairs may be distributed throughout the expandable electrode assembly 30. In some cases, the bipolar electrode pairs may be formed between first and second electrodes 64 located on the same surface of a flexible member or spline 60, between first and second electrodes 64 located on opposite surfaces of a flexible member or spline 60, or between a first electrode 64 located on a first spline 60 and a second electrode 64 located on a second spline 60. In the example in which the bipolar electrode pair is formed between electrodes 64 located on different splines 60, the individual electrodes 64 forming the bipolar electrode pair may be both located on the inner surface of their respective splines 60, the outer surface of their respective splines 60 or, alternatively, one electrode 64 may be located on an outer surface of its respective spline 60 and the other electrode 64 forming the bipolar electrode pair may be located on the inner surface of its respective spline 60. These are just some examples.

In some cases, each of the flexible splines 60 may include at least one bipolar electrode pair. In some cases, all of the electrodes 64 located on the flexible splines 60 may be paired together to form a plurality of electrode pairs distributed along the length of the individual flexible splines 60. In some cases, the electrode pairs may be located equidistant from one another along the length of each of the flexible splines 60. Alternatively, the electrode pairs may have a varied spacing forming an electrode array having an asymmetrical distribution. Up to thirty-two bipolar electrode pairs may be distributed throughout the electrode assembly 30 for a total of up to sixty-four electrodes 64 depending upon the overall size and geometry of the electrode assembly 30. However, it is contemplated that the electrode assembly 30 may be configured such that it is capable of carrying fewer or greater than thirty-two bipolar electrode pairs, depending upon the overall size and geometry of the electrode assembly 30 and the desired application.

Figure 5B:
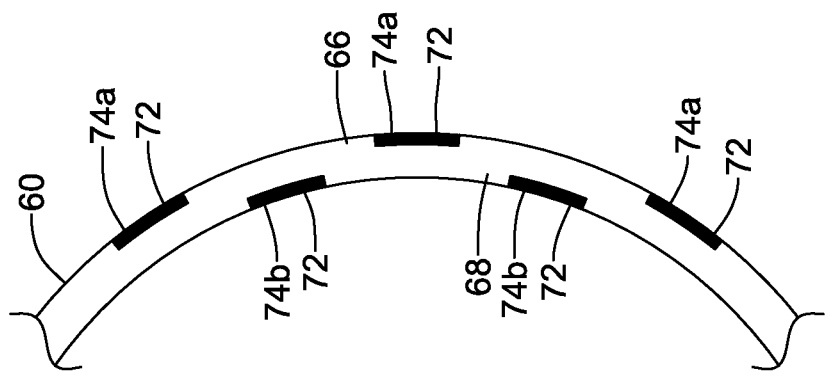
FIGS. 5A and 5B are close-up schematic views of exemplary individual splines of an expandable electrode assembly including multiple bipolar electrode pairs.
Figure 5A:
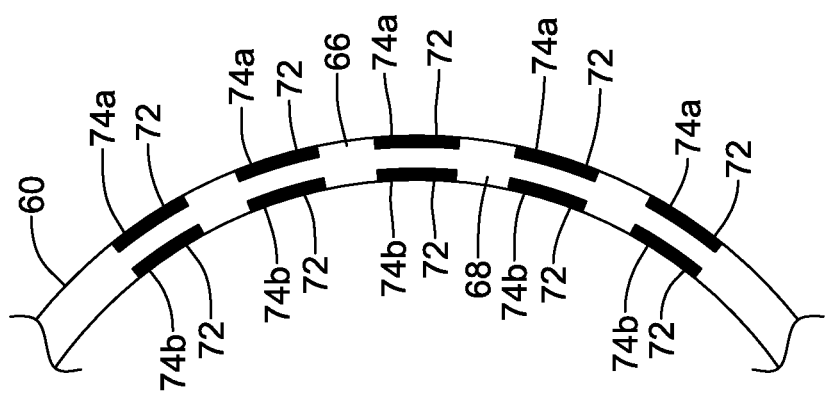

FIGS. 5A and 5B are close-up schematic views of two illustrative individual flexible members or splines 60 including a plurality of bipolar electrode pairs 72 distributed along their length. The orientation of the dipole of the bipolar electrode pair 72 does not affect the ability of the bipolar electrode pair 72 in sensing local electrical activity of the heart. However, it may be useful for the clinical or other individual performing the procedure to know whether the positive or negative electrode of the bipolar pair is located on the outer surface 66 of the flexible splines. It will be generally understood by those skilled in the art that each bipolar electrode pair 72 formed across the flexible splines will have the same electrical orientation. In addition or alternatively, at least some bipolar electrode pairs may be formed between adjacent electrodes on the outer or inner surface 66, 68 of the splines 60 (not shown). It will be generally understood that each of the flexible splines 60 forming the electrode assembly 30 will have a similar if not, the same construction, and in some cases, may be substantially planar or flat.

As shown in FIGS. 5A and 5B, the bipolar electrode pairs 72 may be spaced an equal distance from one another along the length of the spline 60. In some cases, all of the bipolar electrode pairs 72 located along the length of each of the flexible splines 60 of the electrode assembly 30 include a first electrode 74a located on the outer surface 66 and a second electrode 74b located opposite the first electrode 74a on the inner surface 68 of the flexible splines 60. In some cases, as shown in FIG. 5A, the electrodes 74a, 74b forming the bipolar electrode pair 72 may be located directly opposite one another across the spline 60. In addition or alternatively, as shown in FIG. 5B, the electrodes 74a, 74b forming the bipolar electrode pair 72 may be offset from one another such that the electrodes 74a, 74b forming the bipolar electrode pairs 72 along the length of the flexible member or spline 60 have a staggered configuration. In some cases, a first electrode 74a located on an outer surface 66 of a spline 60 may be offset from a second electrode 74b located on the inner surface 68 of the spline 60 by one half the measurable distance between adjacent electrodes 74b located on the inner surface of the spline 60. The reverse may also be true. A first electrode 74b located on the inner surface 68 of the spline 60 may be offset from a second electrode 74a located on the outer surface 66 of the spline 60 by one half the measurable distance between adjacent electrodes 74a located on the outer surface 66 of the spline 60. In other cases, a first electrode 74a, 74b of a bipolar electrode pair 72 may be offset from a second electrode 74a, 74b located on the opposite surface 66 or 68 of the spline 60 by one quarter, one third, two thirds or three quarters of the distance between two adjacent electrodes 74 or 74b located on the opposite surface 66 or 68 of the spline 60. These are just some examples.

Referring back to the example shown in FIG. 5A, a number of advantages may be associated with utilizing multiple bipolar electrode pairs 72 located on each of the splines 60 of the electrode assembly 30 having a first electrode 74a located on the outer surface 66 and a second electrode 74b located opposite the first electrode 74a on the inner surface 68 of each of the flexible splines 60. Because the electrodes 74a, 74b forming a bipolar electrode pair 72 are located on opposite surfaces 66, 68 of the flexible spline 60, they may be spaced closely together, separated only by the thickness of the spline 60. In some cases, the distance between the two electrodes located on the outer and inner surfaces 66, 68 of the splines 60 may be less than about 1.5 mm, less than about 1.0 mm, less than about 0.8 mm, less than about 0.5 mm and more particularly, less than about 0.4 mm. Such minimal spacing between the electrodes 74a, 74b of a bipolar electrode pair 72 may be not be possible if the electrodes 74a, 74b are located on the same surface (outer or inner) of a spline 60.

Placing the electrodes 74a, 74b on opposite surfaces 66, 68 may avoid problems such as increased impedance and susceptibility to noise associated with reducing the size of the electrodes to minimize the distance between adjacent electrodes. For example, if the individual electrodes forming the bipolar pair are located on the same surface (outer or inner surface) of the spline 60, the spacing between the electrodes may be decreased by decreasing the size of the electrodes such that they may be spaced more closely together. However, the reduction in electrode surface area becomes problematic because the reduced electrode surface area results in an increase in impedance. Placing the electrodes on opposite surfaces of the splines may mitigate impedance concerns by allowing a suitable electrode surface area to be maintained while decreasing the spacing between electrodes.

Additionally, the reduced spacing between the electrodes of the bipolar electrode pair 72 resulting from their location on opposite surfaces of a spline 60 may improve the ability of the bipolar electrode pair 72 to reject far field noise, and may facilitate an improved reduction in noise even from nearby, adjacent tissue. The ability to reject far field signals, even those generated by adjacent tissue, may improve the output signal generated by the bipolar pair of electrodes by reducing and localizing the sensing area to the tissue directly adjacent the bipolar electrode pair and more particularly, to the tissue adjacent the electrode located on the outer surface 66 of the spline 60. For example, when the electrodes 74a, 74b of a bipolar electrode pair 72 are located on opposite surfaces of a spline 60, they may sense nearly the identical far field signal such that when an activation signal sensed by the first electrode is subtracted from an activation signal generated by the second electrode of the bipolar electrode pair, any noise or other signal pollution resulting from the far field signal is removed from the resulting bipolar electrogram. In addition, any differences between the two activation signals sensed by the first and second electrodes 74a, 74b of the bipolar electrode pair may be emphasized such as when the electrode located on the outer surface 66 of the spline 60 is in contact with heart tissue. The remaining signal after subtraction may be indicative of the local electrical activation directly adjacent the electrode in contact with the heart tissue. Because the signal may be more localized, this may increase the spatial responsivity of the electrode system which includes multiple bipolar electrode pairs including a first electrode located on an outer surface opposite a second electrode located on an inner surface of spline which are used to sense multiple activation signals in a similar manner to produce a map of the electrical activity of the patient's heart. The improved output signal indicative of the sensed electrical activity generated by the bipolar electrode pair may, in turn, produce an improved bipolar electrogram, and may provide a better representation of the electrodes' location in a three-dimensional space for mapping the electrical activity of the patient's heart.

In addition, because each of the bipolar electrode pairs may be orientated substantially perpendicular to the direction of wavefront propagation which may reduce the sensitivity of the bipolar signal to the direction of wavefront propagation. Additionally, the perpendicular orientation to the direction of wavefront propagation may cause the electrode located on the outer surface of the spline to behave in a unipolar fashion with the electrode located on the inner surface serving substantially as a reference electrode. This phenomenon may be true for each bipolar electrode pair 72 located along the length of the spline 60. Finally, because each of the electrodes of the bipolar electrode pairs 72 are substantially co-located in space, this may result in an improved spatial response pattern to the intrinsic electrical activity of the patient's heart resulting in a more accurate representation (map) of the electrical activity of the patient's heart.

In use, according to some embodiments, bipolar electrograms measured using electrodes 74a, 74b on opposing surfaces 66, 68 of each of the splines 60 can also be used for detecting contact with viable tissue. When the tissue nearest the electrode 74a located on the outer surface 66 is not electrically active or is located far away from the electrode 74a, the signals from the two opposing electrodes 74a, 74b may be substantially identical, and the bipolar electrogram generated by the bipolar electrode pair 72 will have a small amplitude. When tissue is nearest the electrode 74a located on the outer surface 66 and is electrically active, the rapid spatial decay of the local activation will result in a bipolar signal having a large amplitude.

In some embodiments, impedance measurements can also be used to detect and/or confirm tissue contact. The impedance measured separately through opposing electrodes of a bipolar electrode pair 72 may be different because of the medium through which the signal must travel to reach each sensing electrode of the bipolar electrode pair 72. For example, electrode 74a, located on the outer surface 66, may exhibit a greater impedance than electrode 74b, located on the inner surface 68, which may be in contact with mostly blood. A bipolar impedance measurement between the two electrodes may therefore rise sharply with tissue contact, providing a clear and localized indication of tissue contact.

In still other embodiments, to detect tissue proximity rather than just contact, opposing electrodes can be used for a four wire (or more) impedance measurement, with a first pair of electrodes driving current and a second pair of electrodes measuring voltage. For example, current can be driven between at least a first adjacent pair of interior electrodes, and a voltage drop can be measured across a second adjacent pair of exterior electrodes. Tissue proximity will increase the measured voltage due to the lower conductivity of tissue relative to blood. In another example, a current can be driven between a first pair of opposing electrodes and a voltage can be measured using one or more nearby opposing pair of electrodes. The impedance measurements may be repeated for different combinations of electrode pairs. These are just some examples.

The impedance measurements obtained according to the different methods as described herein may be used to determine a distance between the electrode assembly 30 and the heart tissue. Additionally or alternatively, the impedance measurements may be used to weight the different activation times obtained from the bipolar electrograms, and may be used to indicate which activation times correspond to good tissue contact. The impedance measurements also may be used to characterize the tissue being contacted by the different electrodes such as, for example, to confirm whether or not a tissue area of interest has been successfully ablated using the ablation catheter 18.

Figure 6:
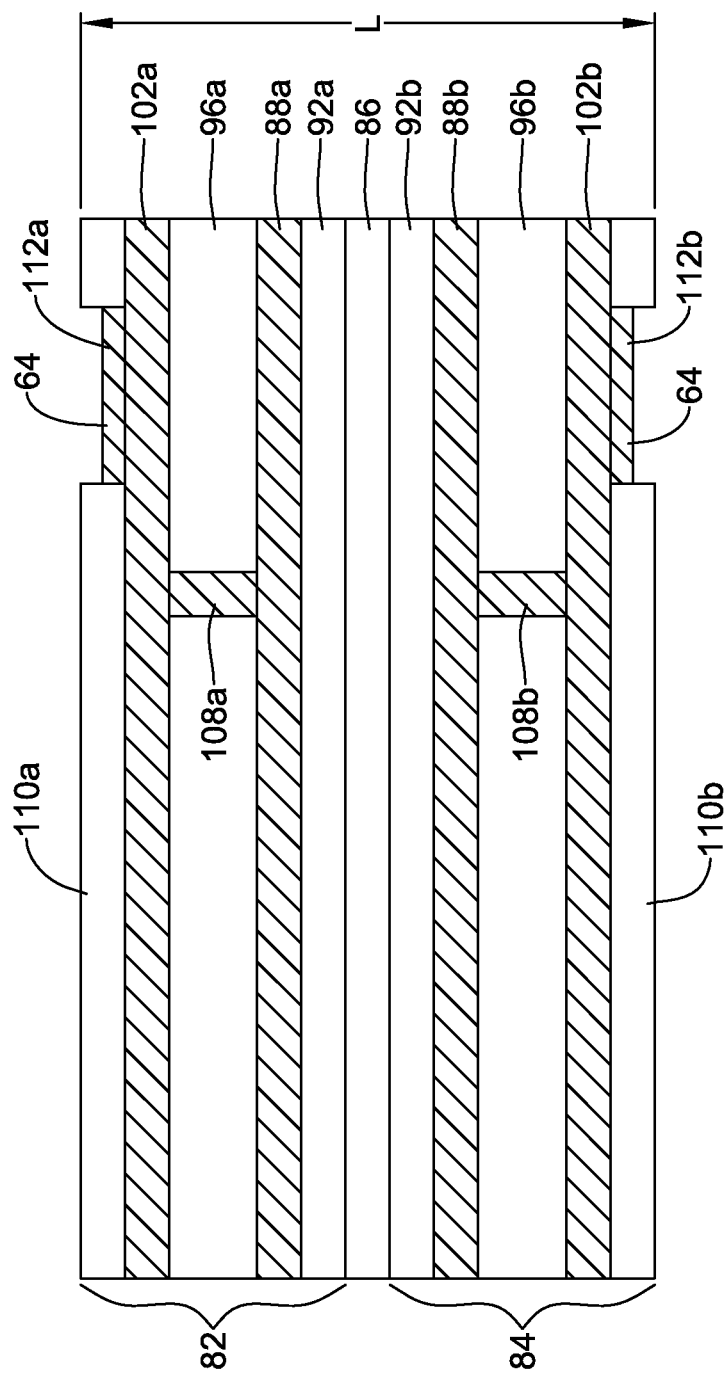
FIG. 6 is a side, cross-sectional view of an exemplary multi-layered flexible sheet including at least one flexible printed circuit used to construct an expandable electrode assembly.

FIGS. 6-9D relate to a method of forming an electrode assembly 30 as described herein. In many cases, the expandable electrode assembly 30, including the flexible splines 60 having multiple electrodes located on the outer and inner surfaces 66, 68 may be constructed from a multi-layered flexible sheet 80 including a first flexible printed circuit 82 adhesively bonded to an upper surface of a substrate and a second flexible printed circuit 84 bonded to a lower surface of the same substrate. The first and second flexible printed circuits 82, 84 define the outer and inner surfaces 66, 68 of each of the splines 60. FIG. 6 is a cross-sectional view of an exemplary multi-layered flexible sheet 80 including the first and second flexible printed circuits 82, 84 from which an expandable electrode assembly 30, as described herein, may be constructed. The total thickness L of the flexible sheet 80, including the two flexible printed circuits 82, 84, is less than about 0.4 mm and defines the thickness of each of the individual splines 60. It will be generally understood that the flexible sheet 80, including the two flexible printed circuits 82, 84, may be fabricated using a variety of suitable known techniques for producing circuits, including flexible printed circuits, having multiple layers. These techniques may include but are not limited to: laminating, masking, photolithography, etching, plating, sputtering, vapor deposition, and/or the like. Similar techniques or combination of techniques may be used to fabricate a single, dual sided flexible printed circuit as is also described herein.

In some cases, the multi-layered flexible sheet 80 may include a relatively stiff substrate 86. The substrate 86 may be constructed from Nitinol or some other stiff material such as a polyimide or polyether ether ketone (PEEK) that may facilitate shape retention of the electrode assembly 30. Alternative materials such as, for example, a compliant material may be used to form the substrate 86 to obtain the desired mechanical characteristics. A first flexible printed circuit 82 defining at least a first electrode may be formed on the upper surface of the substrate 86 and a second flexible printed circuit 84 defining at least a second electrode may be formed on the lower surface of the substrate. In forming each of the first and second flexible printed circuits 82, 84, first metallization layer 88a, 88b may be bonded to the upper and lower surfaces of the substrate 86 using an adhesive layer 92a, 92b. An insulating layer 96a, 96b may be deposited over the first metallization layer 88a, 88b. A second metallization layer 102a, 102b may be formed over the insulating layer 96a, 96b. A connection can be formed by constructing a via between the two metallization layers 88a and 102a and 88b, 102b. A via can be formed by creating a hole through both metallization layers 88, 102 and the insulating layer 96 and then plating the walls of the hole between the two metallization layers 88, 102, to form a metal connection 108a, 108b. A topcoat layer 110a, 110b may then be provided over the outer metallization layers 102a, 102b. The topcoat layer 110a, 110b serves to insulate portions of the outer metallization layer 102a, 102b from external contact. Portions of the topcoat layer 110a, 110b may be removed at selected locations along the flexible printed circuits 82, 84 and an additional metal layer 112a, 112b may be sputter-coated or plated onto the exposed portion of the outer metallization layers 102a, 102b to form the electrodes 64.

The material used to form the electrodes 64 may be selected to reduce impedance of the electrochemical interface between the electrode 64 and blood. Reducing impedance may reduce overall system noise. Exemplary electrode materials include, but are not limited to gold, stainless steel, platinum, platinum-iridium, titanium nitride, platinum black or iridium oxide. In some cases, the electrodes 64 may be fabricated from a gold metal layer coated with iridium oxide.

In some cases, each flexible spline 60 used to form an expandable electrode assembly 30, such as described herein, may be formed from an individual flexible sheet having a first flexible printed circuit formed on an upper surface of substrate and a second flexible printed circuit formed on a lower surface of a substrate. The individual flexible splines 60 may be mechanically joined together to form an expandable electrode assembly 30, as described herein.

Alternatively, the flexible splines 60 may be formed from a single, dual-sided flexible printed circuit having an upper surface including a first electrode of at least one bipolar electrode pair formed therein and a lower surface including a second electrode of the bipolar electrode pair formed therein. It will be generally understood that the single, dual-sided flexible printed circuit may include multiple electrodes formed in the upper and lower surfaces thereof. The electrodes located on opposite surfaces of the splines may define multiple bipolar electrode pairs having a first electrode located on the upper surface of the spline and a second electrode located opposite the first electrode on the lower surface. In some cases, the single, dual-sided flexible printed circuit may include a stiffened core layer. The stiffened core layer may incorporate a shape memory material (e.g. Nitinol) or some other stiff material such as a polyimide or polyether ether ketone (PEEK) that may facilitate shape retention of the electrode assembly 30. Alternative materials such as, for example, a compliant material may be used to form the core layer to obtain the desired mechanical characteristics.

Figure 7A:
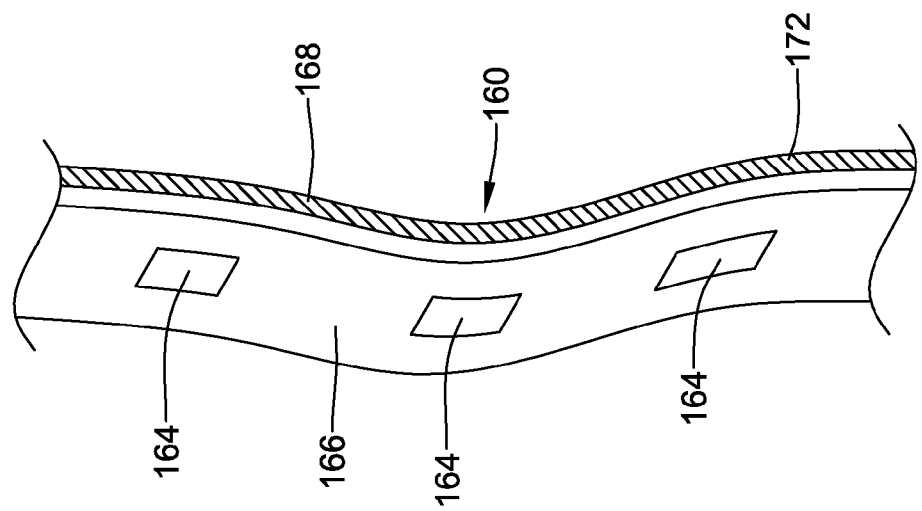
FIGS. 7A and 7B are schematic views of the inner and outer surfaces, respectively, a portion of a flexible spline incorporating a single flexible printed circuit.
Figure 7B:
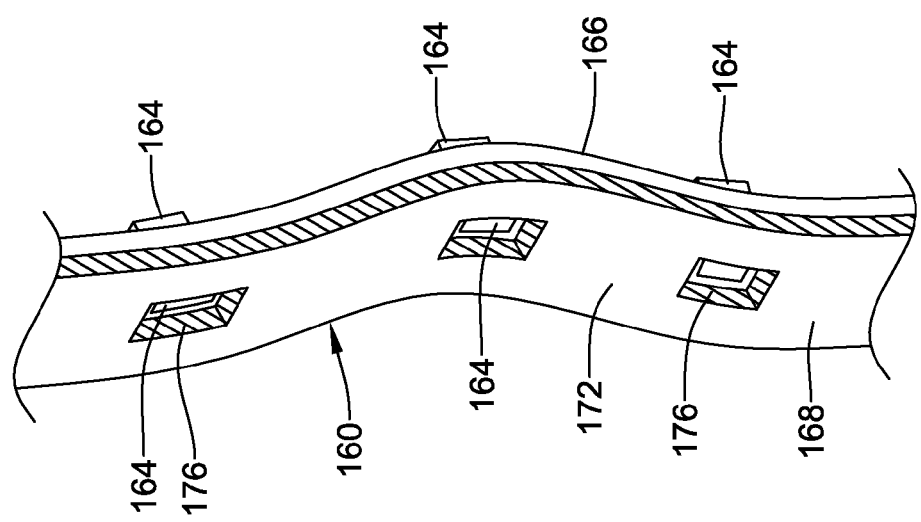

In other cases, the flexible members or splines can also be manufactured from a single, multilayered flexible printed circuit laminated to a mechanical stiffener. FIGS. 7A and 7B show schematic views of the inner and outer surfaces 166, 168 of a portion of a flexible spline 160 incorporating a single flexible printed circuit and a mechanical stiffener 172. The flexible printed circuit may have electrodes 164 formed on both sides of a substrate (e.g. polyimide or PEEK), and may contain multiple conductive layers (e.g. copper or gold or another suitable conductive metal or metal alloy) to route the signal lines from each electrode 160 along the spline 160. A mechanical stiffener 172, fabricated from a suitable metal or plastic material, may be laminated to one side of the flexible printed circuit. The stiffener 172 may feature openings 176 that correspond with the inside electrodes of the flexible circuit, allowing the electrodes 164 to be exposed to the blood pool in vivo and acquire electrical signals.

Figure 8A:
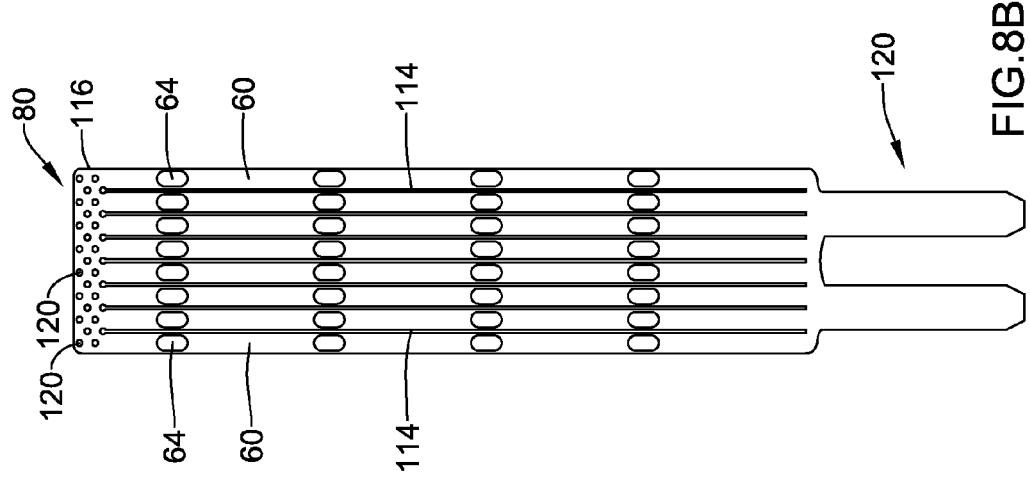
FIG. 8A shows a top plan view of a multi-layered flexible sheet used to construct an electrode assembly.
Figure 8B:
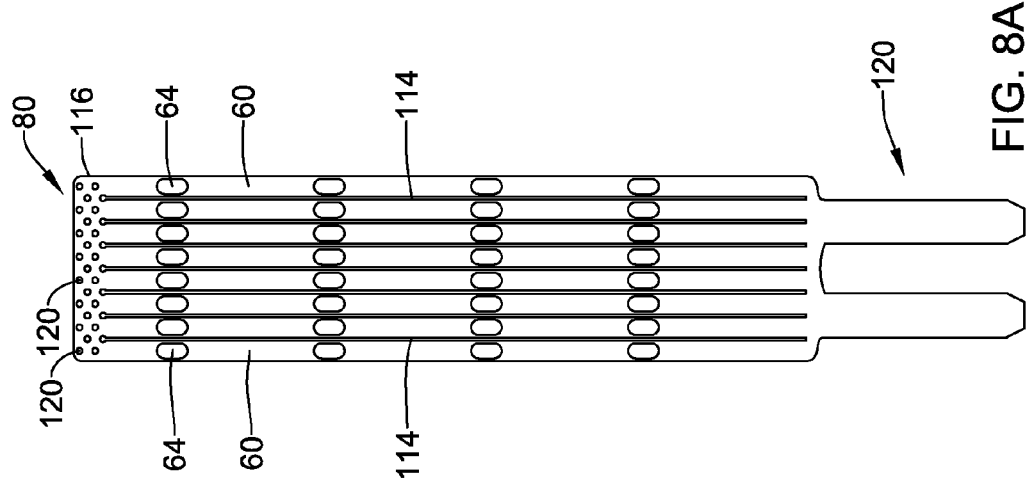
FIG. 8B is a bottom plan view of the multi-layered flexible sheet shown in FIG. 8A.

FIG. 8A shows a top plan view and FIG. 8B is a bottom plan view of a multi-layered flexible sheet used to construct an electrode assembly. FIGS. 9A-9D provide a stepwise illustration of an exemplary method of constructing the expandable electrode assembly from a flexible sheet 80 including two flexible printed circuits 82, 84, as described herein. Starting with a planar, flexible sheet 80, as shown in FIG. 9A, a series of apertures 124 may be formed in a distal region of the flexible sheet 80 using laser cutting, die cutting, chemical etching, or another precision cutting means. Together the plurality of apertures 124 forms a bonding region 116. A termination section 120 may be formed at the opposite end of the flexible sheet 80. The termination section 120 may be used to bond the electrode assembly 30 to the catheter body. Next, as shown in FIG. 9B, the planar flexible sheet 80 may be wound around a major axis 130, bringing first edge 132 toward a second edge 134 of the flexible sheet 80. FIG. 9C shows the two edges 132, 134 juxtaposed with both edges 132, 134 fixed to define a generally cylindrical structure. In some cases, the edges of the distal bonding region 116 may be secured by encapsulating the distal bonding region 116 with an adhesive, and the edges of termination section 120 may be secured by anchoring or bonding it to a distal portion of the catheter body. In some cases, as shown in FIGS. 9A-9D, the termination band may include first and second tabs 136, 138 which may be inserted into a lumen or slot provided in the catheter body and then secured within and adhesive or other suitable bonding technique, and which may include electrical connections to route the electrode signals to the processing system 20 (FIG. 1). FIG. 9D shows the completed electrode assembly 30.

In some cases, the flexible splines 60 may be fully separated from one another such that they are not connected. The distal ends of each of the flexible splines may be mechanically joined together using a band, ring or cap provided for that purpose. In one example, each of the distal ends of the separated splines may be inserted into a corresponding slot provided in a distal cap. The distal ends of the separated splines may be mechanically interlocked with the cap by a locking feature formed at the distal end of the spline. The cap may form an atraumatic tip of the electrode assembly. The proximal ends of the separated splines may be anchored or bonded to a distal end of a catheter body. In some cases, the proximal ends of the separated splines may be first joined together using a band or ring before anchoring or bonding the splines to the distal end of catheter body using an adhesive or potting material.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A catheter comprising:
an elongate catheter body extending from a proximal end to a distal end; and
an expandable electrode assembly disposed at the distal end of the catheter body, the electrode assembly configured to transition from a collapsed configuration to an expanded configuration and comprising at least one flexible member having an outer surface and an inner surface, wherein the at least one flexible member comprises a first electrode disposed on the outer surface of the flexible member and a second electrode disposed on the inner surface of the flexible member, wherein the first electrode and the second electrode are configured to form a bipolar electrode pair and wherein a distance between the first electrode and the second electrode is less than 1.5 mm.

2. The catheter of claim 1, wherein the first electrode is located directly opposite the second electrode.

3. The catheter of claim 1, wherein the first electrode is offset from the second electrode.

4. The catheter of claim 1, further comprising two or more flexible members, each of the two or more flexible members comprising at least a first electrode disposed on the outer surface of the flexible member and at least a second electrode disposed on the inner surface of the flexible member.

5. The catheter of claim 1, wherein the flexible member comprises at least one flexible printed circuit.

6. The catheter of claim 5, wherein the flexible member comprises a single, dual sided flexible printed circuit wherein the first electrode is formed on an outer surface of the flexible printed circuit and the second electrode is formed on an inner surface of the flexible printed circuit.

7. The catheter of claim 1, wherein the distance between the first electrode and the second electrode is less than about 0.5 mm.

8. The catheter of claim 1, wherein the flexible member comprises multiple bipolar electrode pairs defined by a first electrode disposed on the outer surface of a flexible member and a second electrode disposed on the inner surface of the flexible member.

9. A catheter comprising:
an elongate catheter body extending from a proximal end to a distal end;

an expandable electrode assembly disposed at the distal end of the catheter body, the electrode assembly configured to transition from a collapsed configuration to an expanded configuration and comprising two or more flexible splines having an outer surface and an inner surface, wherein at least one of the two or more flexible splines comprises at least a first electrode disposed on the outer surface of the flexible spline and at least a second electrode disposed on the inner surface of the flexible spline, wherein the first electrode and the second electrode are configured to form a bipolar electrode pair and wherein a distance between the first electrode and the second electrode is less than 1.5 mm.

10. The catheter of claim 9, wherein the first electrode is located directly opposite the second electrode.

11. The catheter of claim 9, wherein the first electrode is offset from the second electrode.

12. The catheter of claim 9, wherein each of the two or more splines comprises multiple bipolar electrode pairs defined by a first electrode disposed on the outer surface of a flexible spline and a second electrode disposed on the inner surface of the flexible spline.

13. The catheter of claim 9, wherein each of the two or more flexible splines comprises at least one flexible printed circuit.

14. The catheter of claim 13, wherein the at least one flexible circuit is a single, dual sided flexible printed circuit having a first electrode is formed on an upper surface of the flexible printed circuit and a second electrode formed on a lower surface of the flexible printed circuit.

15. The catheter of claim 13, wherein each of the two or more flexible splines comprises a first flexible printed circuit defining a first electrode formed on an upper surface of a substrate and a second flexible printed circuit defining a second electrode formed on a lower surface of the substrate.

16. A method of forming a flexible electrode assembly, the method comprising:
forming a flexible electrode assembly comprising at least one flexible member having an outer surface and an inner surface, wherein the at least one flexible member comprises a first electrode disposed on the outer surface of the flexible member and a second electrode disposed on the inner surface of the flexible member and wherein the flexible electrode assembly is configured to transition from a collapsed configuration to an expanded configuration, wherein the first electrode and the second electrode are configured to form a bipolar electrode pair and wherein a distance between the first electrode and the second electrode is less than 1.5 mm; and
coupling the flexible electrode assembly to a distal end of an elongate catheter body.

17. The method of claim 16, further comprising:
forming a flexible layered sheet comprising at least one flexible printed circuit defining a first electrode on an outer surface of the flexible layered sheet and a second electrode on an inner surface of the flexible layered sheet;
separating the flexible layered sheet into two or more flexible members, each flexible member having a first electrode located on an outer surface and a second electrode located on an inner surface; and
forming the expandable electrode assembly from at least one of the flexible members.

18. The method of claim 16, further comprising forming an expandable electrode assembly from two or more flexible members by joining the two or more flexible members together at least at a first end of each of the two or more flexible members.

* * * * *